US006852494B2

(12) United States Patent
Liao et al.

(10) Patent No.: US 6,852,494 B2
(45) Date of Patent: Feb. 8, 2005

(54) NUCLEIC ACID AMPLIFICATION

(75) Inventors: Haisun Liao, Sharon, MA (US); Amy Anderson Deik, Wakefield, MA (US); Natalia Mamaeva, West Roxbury, MA (US); Caroline Ngaara Woodward, Boston, MA (US); Shin-Yih Chen, Wellesley, MA (US); Yih Huang, Lexington, MA (US); Ming Shen, Guilford, CT (US); Simon W. Law, Lexington, MA (US); Tai-Nang Huang, Lexington, MA (US)

(73) Assignee: Linden Technologies, Inc., Woburn, MA (US)

( * ) Notice: Subject to any disclaimer, the term of this patent is extended or adjusted under 35 U.S.C. 154(b) by 217 days.

(21) Appl. No.: 10/341,199

(22) Filed: Jan. 10, 2003

(65) Prior Publication Data

US 2004/0137439 A1 Jul. 15, 2004

(51) Int. Cl.[7] ........................... C12Q 1/68; C12P 19/34; C12M 3/00; C12M 1/34; C07H 21/04

(52) U.S. Cl. .......................... 435/6; 435/91.1; 435/91.2; 435/288.3; 435/288.4; 536/23.1; 536/24.3; 536/24.33

(58) Field of Search ............................... 536/24.3, 23.1, 536/24.33; 435/6, 91.1, 91.2, 288.3, 288.4, 287.8, 401, 402, 91.21, 403

(56) References Cited

U.S. PATENT DOCUMENTS

| | | |
|---|---|---|
| 5,130,238 A | 7/1992 | Malek et al. |
| 5,409,818 A | 4/1995 | Davey et al. |
| 5,455,166 A | 10/1995 | Walker |
| 5,480,784 A | 1/1996 | Kacian et al. |
| 5,514,545 A | 5/1996 | Eberwine |
| 5,545,522 A | 8/1996 | Van Gelder et al. |
| 5,554,517 A | 9/1996 | Davey et al. |
| 5,624,825 A | 4/1997 | Walker et al. |
| 5,656,462 A | 8/1997 | Keller et al. |
| 5,712,385 A | 1/1998 | McDonough et al. |
| 5,716,785 A | 2/1998 | Van Gelder et al. |
| 5,723,290 A | 3/1998 | Eberwine et al. |
| 5,766,849 A | 6/1998 | McDonough et al. |
| 5,786,183 A | 7/1998 | Ryder et al. |
| 5,795,715 A | 8/1998 | Livache et al. |
| 5,824,518 A | 10/1998 | Kacian et al. |
| 5,854,033 A | 12/1998 | Lizardi |
| 5,856,088 A | 1/1999 | McDonough et al. |
| 5,888,779 A | 3/1999 | Kacian et al. |
| 5,891,636 A | 4/1999 | Van Gelder et al. |
| 5,908,744 A | 6/1999 | McAllister et al. |
| 5,932,451 A | 8/1999 | Wang et al. |
| 5,958,688 A | 9/1999 | Eberwine et al. |
| 6,004,752 A | 12/1999 | Loewy et al. |
| 6,027,913 A | 2/2000 | Sommer |

(List continued on next page.)

FOREIGN PATENT DOCUMENTS

| | | |
|---|---|---|
| EP | 0 368 906 B1 | 5/1990 |
| WO | WO 88/10315 | 12/1988 |
| WO | WO 89/01050 | 2/1989 |
| WO | WO 89/07149 | 8/1989 |

OTHER PUBLICATIONS

Abbott et al., "Enzymatic Gene Amplification: Qualitative and Quantitative Methods for Detecting Proviral DNA Amplified in Vitro", *Journal of Infectious Diseases* 158(6):1158–1169 (1988).

Baugh et al., "Quantitative analysis of mRNA amplification by in vitro transcription", *Nucleic Acids Research* 29(5):1–9 (2001).

Hirschhorn et al., "SBE–TAGS: An array–based method for efficient single–nucleotide polymorphism genotyping", *PNAS* 97(22):12164–12169 (2000).

Kwoh et al., "Transcription–based amplification system and detection of amplified human immunodeficiency virus type 1 with a bead–based sandwich hybridization format", *Proc. Natl. Acad Sci. USA* 86:1173–1177 (1989).

"List of sequence tags", http://www–genome.wi,mit.edu/publications/SBE–TAGS/, printed Jul. 21, 2002.

"MessageAmp aRNA Kit *Instruction Manual*", v. 0302, Ambion Inc., Jan. 2003.

Milligan et al., "Oligoribonucleotide synthesis using T7 RNA polymerase and synthetic DNA templates", *Nucleic Acids Res* 15(21):8783–8799 (1987).

Murakawa et al., "Laboratory Methods: Direct Detection of HIV–1 RNA from AIDS and ARC Patient Samples", *DNA* 7(4):287–295 (1988).

Novagen brochure, "Strandase Kit", from a pdf document dated Aug. 2, 1999.

"NucleoLink Procedure for Solid Phase–PCR (DIAPOPS)", *TechNote* 5(36), from a pdf document dated 2001.

Poirier and Erlander, "Postdifferential Display: Parallel Processing of Candidates Using Small Amounts of RNA", *METHODS: A Companion to Methods in Enzymology* 16:444–452 (1998).

Sadhu et al., "In vitro synthesis of double stranded RNA and measurement of thermal stability: effect of base composition, formamide and ionic strength", *Biochemistry International* 14(6):1015–1022 (1987).

Sarkar and Sommer, "Access to a Messenger RNA Sequence or Its Protein Product Is Not Limited by Tissue or Species Specificity", *Science* 244:331–334 (1989).

Stoflet et al., "Genomic Amplification with Transcript Sequencing", *Science* 239:491–494 (1988).

*Primary Examiner*—Kenneth R. Horlick
*Assistant Examiner*—Cynthia Wilder
(74) *Attorney, Agent, or Firm*—Fish & Richardson P.C.

(57) ABSTRACT

Disclosed is an insoluble support that can be used, for example, for producing replicates of sample nucleic acids. The support includes a plurality of attached oligonucleotides that include a prokaryotic promoter sequence and a target annealing sequence 3' of the promote. The proximal end of the promoter sequence is spaced from the insoluble support by a distance greater than 10 nm.

11 Claims, 14 Drawing Sheets

U.S. PATENT DOCUMENTS

| | | |
|---|---|---|
| 6,066,457 A | 5/2000 | Hampson et al. |
| 6,132,997 A | 10/2000 | Shannon |
| 6,143,495 A | 11/2000 | Lizardi et al. |
| 6,248,521 B1 | 6/2001 | Van Ness et al. |
| 6,291,170 B1 | 9/2001 | Van Gelder et al. |
| 6,326,173 B1 | 12/2001 | Edman et al. |
| 6,379,932 B1 | 4/2002 | Arnold et al. |
| 6,589,734 B1 | 7/2003 | Kacian et al. |
| 2001/0053541 A1 | 12/2001 | Su et al. |
| 2002/0061533 A1 | 5/2002 | van Gemen |
| 2002/0076716 A1 | 6/2002 | Sabanayagam et al. |
| 2003/0099937 A1 * | 5/2003 | Law .............................. 435/5 |

* cited by examiner

NUCLEIC ACID AMPLIFICATION

BACKGROUND

Genetic information can be analyzed for a number of applications, including medical diagnosis, genotyping, and forensics. The high throughput analysis of nucleic acid samples is facilitated by nucleic acid amplification.

A variety of techniques can be used for nucleic acid amplification. The polymerase chain reaction (PCR; Saiki, et al. (1985) Science 230, 1350–1354) and ligase chain reaction (LCR; Wu. et al. (1989) Genomics 4, 560–569; Barringer et al. (1990), Gene 1989, 117–122; F. Barany. 1991, Proc. Natl. Acad. Sci. USA 1988, 189–193) utilize cycles of varying temperature to drive rounds of synthesis. Transcription-based methods utilize RNA synthesis by RNA polymerases to amplify nucleic acid (U.S. Pat. Nos. 6,066, 457, 6,132,997, and 5,716,785; Sarkar et al., Science (1989) 244:331–34; Stofler et al., Science (1988) 239:491). NASBA (U.S. Patent Nos. 5,130,238; 5,409,818; and 5,554,517) utilizes cycles of transcription, reverse-transcription, and RNaseH-based degradation to amplify a DNA sample. Still other amplification methods include rolling circle amplification (RCA; U.S. Pat. Nos. 5,854,033 and 6,143,495) and strand displacement amplification (SDA; U.S. Pat. Nos. 5,455,166 and 5,624,825).

SUMMARY

The invention is based, in part, on the discovery of a transcription-based method for amplifying nucleic acid s. The method uses an immobilized oligonucleotide that includes a promoter and a target annealing region. The promoter is spaced by a predetermined distance from the insoluble support, e.g., by a distance that enables efficient transcription of the target sequence. The predetermined dista nce can depe nd on the particular reaction conditions, for ex ample, the type of insoluble support, promoter, and attachment between the oligonucleotide and the support.

A ccordingly, in one aspect, the invention features a method that includes: providing an insoluble support including attached oligonucleotides, wherein (1) the attached oligonucleotides include a promoter sequence and a target annealing sequence, and (2) the proximal end of the promoter sequence is spaced from the insoluble support by a distance greater than 5 nm or 10 nm, annealing sample nucleic acids to the attached oligonucleotides; constructing template nucleic acids by extending the attached oligonucleotides using a polymerase; and transcribing the template nucleic acids to produce RNA replicates of the sample nucleic acids. For example, the distance can be between 10 to 150 nm or 10 and 50 nm.

In one embodiment, the attached oligonucleotides each include a ligand 5' of the promoter (e.g., at the 5' terminus), are attached to the insoluble support by a non-covalent interaction (e.g., a ligandfligand-binding protein interaction), and the proximal end of the promoter is between 5–30, 6–18, or 6–12 nucleotides from the ligand, e.g., from the 5' terminus. For example, the attached oligonucleotides include a biotin moiety (e.g., at the 5' terminus), are attached to the insoluble support by a biotin/biotin-binding protein interaction (e.g., avidin or streptavidin), and the proximal end of the promoter is at least 5 nucleotides, e.g., between 5–30 nucleotides from the biotin moiety.

In another embodiment, the attached oligonucleotides are attached to the insoluble support by a polyethylene glycol linker that has at least 8 units or between 8–20 or 8–16 units, by a chemical linker having a main chain length including the same number of main chain atoms as the polyethylene glycol linker or having the same physical length as the polyethylene glycol linker.

In another embodiment, the attached oligonucleotides are covalently attached at their 5' terminus, and the proximal end of the promoter is between 12–50, 20–35, or 23–28 nucleotides from the 5' terminus of each of the attached oligonucleotides.

The sample nucleic acids include RNA, DNA, PNA, or other nucleic acid molecules.

The constructing can include extending the attached oligonucleotide using an RNA-directed DNA polymerase to produce an extended stranded and synthesizing a DNA strand complementary to the extended strand to produce complementary strands, e.g., by a method described herein. The attached and complementary strands anneal, thereby providing the template nucleic acids.

The method can include joining an adaptor that includes a tag sequence to the double-stranded template. The adaptor can include a promoter sequence, e.g., a prokaryotic promoter sequence. For example, the adaptor includes double-stranded DNA.

The promoter sequence can be a prokaryotic promoter sequence, e.g., a bacteriophage promoter sequence, e.g., a T7, T3, or SP6 promoter sequence. In one embodiment, at least some of the attached oligonucleotides include a promoter and a homopolymeric T tract. These attached oligonucleotides can further include a 3' terminal A, G, or C.

The distance between the proximal end of the promoter sequence and the insoluble support can be sufficient to enable at least 2, 4, 8, or 16 times the yield (e.g., between 2 and 32 times) of replicate RNAs as obtained using a distance of less than 2 nm between the proximal end of the promoter sequence and the insoluble support.

In another aspect, the invention features a method that includes: providing an insoluble support including attached template nucleic acids (e.g., covalently or non-covalently attached), wherein (1) each attached template nucleic acids include a promoter sequence and a target sequence, and (2) the proximal end of the promoter sequence is spaced from the insoluble support by a predetermined distance; and transcribing the template nucleic acids to produce RNA replicates of the sample nucleic acids. For example, the distance between the proximal end of the promoter sequence and insoluble support can be between 10 to 150 nr or 10 and 50 nm.

In one embodiment, the attached template nucleic acids each include a ligand 5' of the promoter (e.g., at the 5' terminus), are attached to the insoluble support by a non-covalent interaction (e.g., a ligand/ligand-binding protein interaction), and the proximal end of the promoter is between 5×30, 6–18, or 6–12 nucleotides from the ligand, e.g., from the 5' terminus. For example, the attached templates include a biotin moiety (e.g., at the 5' terminus), are attached to the insoluble support by a biotin/biotin-binding protein interaction (e.g., avidin or streptavidin), and the proximal end of the promoter is at least 5 nucleotides, e.g., between 5–30 nucleotides from the biotin moiety.

In another embodiment, the attached template nucleic acids are attached to the insoluble support by a polyethylene glycol linker that has at least 8 units or between 8–20 or 8–16 units, by a chemical linker having a main chain length including the same number of main chain atoms as the polyethylene glycol linker or having the same physical length as the polyethylene glycol linker.

In another embodiment, the attached template nucleic acids are covalently attached at their 5' terminus, and the proximal end of the promoter is between 12–50, 20–35, or 23–28 nucleotides from the 5' terminus of each of the attached template nucleic acids.

The template nucleic acids can further include a second promoter positioned to transcribe a nucleic acid segment located between the first and second promoters. Each is configured to transcribe a strand of the nucleic acid segment such that both strands of the nucleic acid segment are transcribed. This method includes transcribing the template nucleic acid using the first and second promoters to produce RNA complementary to each strand, and recovering double-stranded RNA for the nucleic acid segment.

The template nucleic acids can correspond to nucleic acids in a biological sample, e.g., a sample of nucleic acids obtained from a cell, e.g., from a culture cell, tissue, free-living cell or organism. The template nucleic acids can include regions that represent nucleic acids in the sample in comparable proportions. For example, the template nucleic acids can correspond to eukaryotic mRNAs, genomic DNAs, and so forth.

In one embodiment, a plurality of the template nucleic acids each comprises a common adaptor sequence at their respective distal ends. The adaptor sequence can include a promoter sequence.

In another aspect, the invention features a method of archiving a sample of complex nucleic acids. The method includes: providing a first insoluble support having 5' attached oligonucleotide, wherein the attached oligonucleotide includes a promoter sequence that is at least 4 nm from the insoluble support; annealing a complex sample that includes sample nucleic acids to the insoluble support; and producing template nucleic acids immobilized on the insoluble support that each include at least a segment of the sample nucleic acids, the immobilized templates representing the composition of the sample nucleic acids; transcribing the template nucleic acids from the insoluble support; archiving the insoluble support; and transcribing the template nucleic acids from the insoluble support. For example, the distance can be between 10 to 150 nm or 10 and 50 nm.

In one embodiment, the attached oligonucleotides each include a ligand 5' of the promoter (e.g., at the 5' terminus), are attached to the insoluble support by a non-covalent interaction (e.g., a ligand/ligand-binding protein interaction), and the proximal end of the promoter is between 5–30, 6–18, or 6–12 nucleotides from the ligand, e.g., from the 5' terminus. For example, the attached oligonucleotides include a biotin moiety (e.g., at the 5' terminus), are attached to the insoluble support by a biotin/biotin-binding protein interaction (e.g., avidin or streptavidin), and the proximal end of the promoter is at least 5 nucleotides, e.g., between 5–30 nucleotides from the biotin moiety.

In another embodiment, the attached oligonucleotides are attached to the insoluble support by a polyethylene glycol linker that has at least 8 units or between 8–20 or 8–16 units, by a chemical linker having a main chain length including the same number of main chain atoms as the polyethylene glycol linker or having the same physical length as the polyethylene glycol linker.

In another embodiment, the attached oligonucleotides are covalently attached at their 5' terminus, and the proximal end of the promoter is between 12–50, 20–35, or 23–28 nucleotides from the 5' terminus of each of the attached oligonucleotides.

The template nucleic acids can correspond to nucleic acids in a biological sample, e.g., a sample of nucleic acids obtained from a cell, e.g., from a culture cell, tissue, free-living cell or organism. The template nucleic acids can include regions that represent nucleic acids in the sample in comparable proportions. For example, the template nucleic acids can correspond to eukaryotic mRNAs, genomic DNAs, and so forth.

The invention also features insoluble supports and immobilized oligonucleotides described herein, e.g., including one or more features described herein. The insoluble supports can include template nucleic acids, e.g., including features acquired from a sample described herein.

In another aspect, the invention features an insoluble support that includes a plurality of attached oligonucleotides, wherein (1) the attached oligonucleotides include a prokaryotic promoter sequence and a target annealing sequence, (2) the target annealing sequence is 3' of the promoter, (3) the oligonucleotide has an extendable 3' terminus; and (4) the proximal end of the promoter sequence is spaced from the insoluble support by a distance greater than 10 nm.

In one embodiment, the oligonucleotides are less than 80 nucleotides in length.

In one embodiment, each target annealing sequence of the plurality is the same and the target annealing sequence can anneal to a plurality of different target sequences. For example, the target annealing sequence can include a poly-thymidine tract. Each target annealing sequence of the plurality can include a poly-thymidine tract and a terminal 3' A, G, or C.

In one embodiment, target nucleic acids are annealed to the support, e.g., target nucleic acids from a sample described herein.

In one embodiment, the attached oligonucleotides each include a ligand 5' of the promoter (e.g., at the 5' terminus), are attached to the insoluble support by a non-covalent interaction (e.g., a ligand/ligand-binding protein interaction), and the proximal end of the promoter is between 5–30, 6–18, or 6–12 nucleotides from the ligand, e.g., from the 5' terminus. For example, the attached oligonucleotides include a biotin moiety (e.g., at the 5' terminus), are attached to the insoluble support by a biotin/biotin-binding protein interaction (e.g., avidin or streptavidin), and the proximal end of the promoter is at least 5 nucleotides, e.g., between 5–30 nucleotides from the biotin moiety.

In another embodiment, the attached oligonucleotides are attached to the insoluble support by a polyethylene glycol linker that has at least 8 units or between 8–20 or 8–16 units, by a chemical linker having a main chain length including the same number of main chain atoms as the polyethylene glycol linker or having the same physical length as the polyethylene glycol linker.

In another embodiment, the attached oligonucleotides are covalently attached at their 5' terminus, and the proximal end of the promoter is between 12–50, 20–35, or 23–28 nucleotides from the 5' terminus of each of the attached oligonucleotides.

In another aspect, the invention features an insoluble support that includes attached template nucleic acids, wherein (1) each attached template nucleic acids include a prokaryotic promoter sequence, a target sequence, and a ligand (2) for each template nucleic acid, the promoter is located between the target sequence and ligand, (3) the template nucleic acids can be transcribed to produce RNA copies of each respective target sequence, (4) the ligand is bound to a ligand-binding protein immobilized on the support, and (5) the proximal end of the promoter sequence is spaced from the ligand between 5 and 30 nucleotides.

In a related aspect, the support includes attached template nucleic acids, wherein (1) each attached template nucleic acids include a prokaryotic promoter sequence and a target sequence, (2) for each template nucleic acid, the promoter is located between the target sequence and the site that attaches the template nucleic acid to the support, (3) the template nucleic acids can be transcribed to produce RNA copies of each respective target sequence, and (4) the template nucleic acids is spaced from the support by a nucleotide-free linker that includes an identical number of main chain atoms as a polyethylene glycol linker that has at least 8 units or between 8 and 16 units.

In another related aspect, the support includes attached template nucleic acids, wherein (1) each attached template nucleic acids include a prokaryotic promoter sequence and a target sequence, (2) for each template nucleic acid, the promoter is located between the target sequence and the site that attaches the template nucleic acid to the support, (3) the template nucleic acids can be transcribed to produce RNA copies of each respective target sequence, and (4) the attached template nucleic acids are covalently attached to the support, and the proximal end of the promoter is between 12 and 50 nucleotides from the 5' terminus of each of the oligonucleotides.

The template nucleic acids can correspond to nucleic acids in a biological sample, e.g., a sample of nucleic acids obtained from a cell, e.g., from a culture cell, tissue, free-living cell or organism. The template nucleic acids can include regions that represent nucleic acids in the sample in comparable proportions. For example, the template nucleic acids can correspond to eukaryotic mRNAs, genomic DNAs, and so forth.

In one embodiment, a plurality of the template nucleic acids each comprises a common adaptor sequence at their respective distal ends. The adaptor sequence can include a promoter sequence.

In another aspect, the invention features a method that includes: cleaving sample nucleic acids to yield cleaved nucleic acids; treating the cleaved nucleic acids using a nuclease that preferentially digests double stranded nucleic acid relative to single stranded nucleic acid to yield treated sample nucleic acids; annealing an oligonucleotide to the treated sample nucleic acids, the oligonucleotide (also referred to as the "SSP oligonucleotide") having a promoter region and a target binding region that binds to a first target site; and transcribing the annealed treated sample nucleic acid using an RNA polymerase that recognizes the promoter region to generate RNA replicates of the sample nucleic acid. The SSP oligonucleotide can include an element that spaces the promoter from the insoluble support, e.g., by a distance described herein. The method is useful for amplifying sample nucleic acid.

In one embodiment, the method further includes, prior to or concurrent with the transcribing, extending the annealed oligonucleotide and/or the annealed sample nucleic acid using a DNA polymerase. The DNA polymerase can lack 3' to 5' exonucleases activity. For example, the DNA polymerase can be the Klenow fragment of $E.$ $coli$ DNA polymerase I, or a modified or unmodified bacteriophage DNA polymnerase such as SEQUENASE™. In one embodiment, the method includes separating the extended strands from the unannealed and/or unextended sample nucleic acid strands prior to transcription. In another embodiment, only the annealed sample nucleic acid is extended, i.e., thereby rendering the promoter region double stranded and functional. The SSP oligonucleotide can have a 3' modification that prevents its extension.

The promoter region and the target binding region of the SSP oligonucleotide are described herein below.

In one embodiment, the SSP oligonucleotide includes a moiety that is attachable to receiving agent. The receiving agent can be attached to an insoluble support, e.g., a bead or planar surface. In one embodiment, the moiety and receiving agent are members of a specific binding pair, e.g., biotin and avidin (or streptavidin), sugar and lectin, and so forth. In another embodiment, the moiety and receiving agent are chemically reactive with each other. For example, the moiety can be an amino group and the receiving agent can be an activated group that includes an electron-withdrawing group on an N-substituted sulfonamide.

The method can be performed at temperatures of less than about 50, 45, or 40° C. In other words, in some implementations, the reaction temperature never exceeds these temperatures. The method can be performed under isothermal or substantially isothermal conditions. Further enzymes used in one or more reactions can be added and removed by flowing or otherwise altering the medium that contacts the insoluble support. In one embodiment, pins or other devices that include the SSP oligonucleotide immobilized thereto can be moved from one reaction mixture to another.

The cleaving can include shearing, sonication, or digestion using a cleaving agent such as an endonuclease, e.g., one or more restriction endonucleases. The restriction endonucleases can specifically recognize a 4, 5, or 6 base pair site. They can digest DNA to produce recessed ends, e.g., 5' overhangs, or blunt ends. The sample nucleic acid can be, for example, DNA or RNA. In a preferred embodiment, the sample nucleic acid is DNA, e.g., genomic DNA, cDNA, or recombinant DNA.

The cleaving can generate fragments having an average size of less than about 2000, 1000, 700, or 500 nucleotides or can generate a fragment in a region of interest of less than about 2000, 1000, 700, or 500 nucleotides. The method can include inactivating the cleaving agent and/or separating the cleaved nucleic acids from the cleaving agent.

The nuclease that is used to treat the cleaved nucleic acid preferentially digests double stranded nucleic acid relative to single stranded nucleic acid. A preferential digestion as used herein, refers to at least a 50-fold difference in $K_m$ for the respective substrates. The nuclease can be highly processive. The nuclease can be an exonuclease, e.g., lambda exonuclease or T7 exonuclease.

The nuclease can be attached to an insoluble support, e.g., a bead, such as a paramagnetic bead. The method can further include separating the nuclease from the treated sample nucleic acids. The method can include inactivating the nuclease.

The method can further include reverse transcribing the RNA replicates and/or treating the RNA replicates using a ribonuclease, e.g., RNaseH. In another embodiment, the method can further include translating the RNA replicates. In still another embodiment, the method can further include analyzing the RNA replicates or DNA copies thereof. The analysis can include determining the identity of a nucleotide or the sequence of a region. The analysis can indicate whether an allele or polymorphism is present.

In another aspect, the invention features a method that includes: providing an insoluble support having a plurality of addresses; at each of the plurality of addresses, depositing or synthesizing an oligonucleotide that includes a 5' promoter region and a 3' target binding region that is complementary to a target site; contacting a sample of nucleic acid to the insoluble support; for each of the oligonucleotides of the plurality of addresses, permitting the target binding region to anneal to its target site in the sample, if present; extending the annealed sample nucleic acid using a DNA polymerase (e.g., thereby rendering the promoter region of the oligonucleotide double-stranded); and transcribing the annealed sample nucleic acid using an RNA polymerase that recognizes the promoter region. The oligonucleotide can include an element that spaces the promoter from the insoluble support, e.g., by a distance described herein.

In one embodiment, the promoter regions are the same among the oligonucleotides of the plurality of addresses. In another embodiment, the promoter regions are different.

The method can include, prior to the extending or the transcribing, separating unannealed sample nucleic acids or separate annealed and unannealed sample nucleic acids (e.g., after extending the annealed oligonucleotides to copy).

In one embodiment, the oligonucleotide is extended using a DNA polymerase.

In another embodiment, the insoluble support is positioned in a flow chamber. The RNA polymerase and ribonucleotides are provided to the chamber as transcription products are removed from the chamber.

In still another aspect, the invention provides a method that includes: providing an insoluble support having a plurality of addresses, each address including (1) a first nucleic acid segment having (a) a 5' promoter region and (b) a variable 3' target binding region, and (2) a second nucleic acid segment that binds the 5' promoter region; annealing sample nucleic acids to the insoluble support; joining the 5' terminus of the second nucleic acid segment to the 3' end of the annealed sample nucleic acid; optionally removing unjoined and/or unannealed sample nucleic acids; and transcribing the joined sample nucleic acids using an RNA polymerase that recognizes the 5' promoter region. The first nucleic acid segment can include an element that spaces the promoter from the insoluble support, e.g., by a distance described herein.

In one embodiment, the first nucleic acid segment and the second nucleic acid segment are segments of a single nucleic acid strand, e.g., a hairpin strand. The hairpin can include a modified nucleotide or backbone position in the hairpin loop. The modification includes a moiety that is attached to the insoluble support. The position of the hairpin can be selected such that the 5' end of the promoter region is spaced from the insoluble support, e.g., by a distance described herein.

The joining can be effected by a ligase, e.g., T4 DNA ligase, or a thermostable ligase. A thermostable ligase can be useful for annealing at temperatures above 40° C. in order to increase annealing specificity.

In one embodiment, the method includes storing or archiving the insoluble support. The insoluble support can be stored any time after the joining of the annealed sample nucleic acid, e.g., prior to the transcribing, or after the transcribing.

In another aspect, the invention provides a method of analyzing genetic polymorphisms. The method includes: for each polymorphism, locating a fragment flanked by restriction enzyme sites and including the polymorphism such that the sites are less than about 2000, 1000, 700, 500 nucleotides apart; synthesizing a promoter oligonucleotide having (a) a 5' promoter region and (b) a variable 3' target binding region, the variable 3' target binding region being near or flanking one of fragment termini; optionally attaching the promoter oligonucleotide to an insoluble support; annealing sample nucleic acid to the promoter oligonucleotides; contacting a DNA polymerase to the annealed sample nucleic acids to extend the annealed sample nucleic acid and render the promoter double-stranded; and transcribing the extended annealed sample nucleic acid using an RNA polymerase specific for the promoter.

In another aspect, the invention provides a method of analyzing genetic polymnorphisms. The method includes: for each polymnorphism, synthesizing a promoter oligonucleotide on an insoluble support, the promoter oligonucleotide having (a) a 5' terminus attached to the support; (b) a 5' promoter region and (c) a variable 3' target binding region, the variable 3' target binding region being within 1000 nucleotides (e.g., less than 800, 700, 500, or 400 nucleotides) of the polymorphism; annealing sample nucleic acid to the promoter oligonucleotides; contacting a DNA polymerase to the annealed sample nucleic acids to extend the annealed sample nucleic acid and render the promoter double-stranded; and transcribing the extended annealed sample nucleic acid using an RNA polymerase specific for the promoter. The promoter oligonucleotide can include an element that spaces the promoter from the insoluble support, e.g., by a distance described herein.

In another aspect, the invention features a method of amplifying a nucleic acid strand. The method includes: annealing a nucleic acid strand to a first oligonucleotide that binds to the strand; extending the strand 3' end to form a first oligonucleotide-strand complex; transcribing the first oligonucleotide-strand complex using a first RNA polymerase to yield a first RNA strand; annealing the first RNA to a second oligonucleotide that binds to the first RNA strand; reverse transcribing the first RNA to yield to a first copy strand; rendering the first copy strand double-stranded to form a second oligonucleotide-copy strand complex or annealing a third oligonucleotide that is complementary to the promoter region of the second oligonucleotide; and transcribing the second oligonucleotide-copy strand complex.

The first oligonucleotide includes a promoter region, specifically recognized by a first RNA polymerase, and a target binding region that binds the strand 3' end. The second oligonucleotide includes a promoter region, specifically recognized by a second RNA polymerase, and a target binding region that binds the first RNA strand 3' end. The first and second oligonucleotides can bind to their targets near the target 3' end, e.g., at a location with the strand terminus, or located near the strand terminus within 25% of the length of the strand. The first and/or second oligonucleotide can include a spacer, e.g., that separates the promoter and the support attachment site by a distance described herein.

The method can be performed in a homogenous reaction mixture.

In another aspect, the invention features a kit that includes: (1) a prokaryotic RNA polymerase; (2) a DNA polymerase that lacks 3' to 5' exonuclease activity; and (3) an exonuclease that is processive and that preferentially digests double stranded nucleic acid relative to single stranded nucleic acid.

The kit can further include: a promoter oligonucleotide that includes (a) a 5' promoter region that is recognized by the prokaryotic RNA polymerase and (b) a variable 3' target binding region. In another embodiment, the kit includes a plurality of promoter oligonucleotides. In another embodiment, the kit includes an insoluble support that is attached to the promoter oligonucleotide or promoter oligonucleotides. The promoter oligonucleotides can include an element that spaces the 5' end of the promoter form the support by a distance described herein.

In another embodiment, the kit further includes ribonucleotides and/or deoxyribonucleotides. In yet another embodiment, the kit further includes a container that includes a plurality of restriction endonucleases. The kit can further one or more reaction containers, e.g., microtiter plates, strips, wells, cassettes, and microfluidic devices.

In another aspect, the invention features a pool of non-naturally occurring RNA strands.

The RNA strands are less than about 1000, 700, or 500 nucleotides in length. In one embodiment, at least some or all of the RNA strands have a nucleic acid sequence which is absent from fully processed mRNA. For example, the RNA strands can be transcribed from fragments of genomic DNA which include introns and/or regulatory regions, e.g., transcriptional regulatory regions. The RNA strands can include a common 5' end, e.g., corresponding to a linker sequence from an SSP oligonucleotide. The common 5' end can be about 2 to 50 nucleotides in length. The 5' end can include an internal ribosome entry site, an initiator methionine, and so forth. The RNA can be uncapped.

In still another aspect, the invention features a reaction mixture that includes: (1) a prokaryotic RNA polymerase; and (2) a plurality of oligonucleotides, each oligonucleotide including (a) a 5' promoter region that is recognized by the prokaryotic RNA polymerase and (b) a variable 3' target binding region. The mixture can further include: (3) ribonucleotides. In another embodiment, the mixture further includes: (4) a DNA polymerase that lacks 3' to 5' exonuclease activity; and (5) deoxyribonucleotides. In one embodiment, the mixture can be used to support a homogeneous reaction in which DNA and RNA are synthesized.

The reaction mixture can further include a second RNA polymerase and a second plurality of oligonucleotides, each of the oligonucleotides including (a) 5' promoter region that recognized by the second RNA polymerase, and (b) a variable 3' target binding region.

In one embodiment, the target binding region of the oligonucleotides of the second plurality can bind to a strand complementary to that bound the target binding region of an oligonucleotide of the first plurality. The two respective target binding regions can be within about 4, 2, 1, 0.7, 0.5, 0.3, or 0.1 kb of one another.

In still another aspect, the invention features an insoluble support that includes a plurality of addresses, each address of the plurality having attached thereto an oligonucleotide that has (a) a 5' promoter region that is recognized by a prokaryotic RNA polymerase and (b) a variable 3' target binding region. The variable target binding region can be between about 12 and 50 nucleotides in length. The target binding region can have a $T_m$ for annealing to its target of between about 24° C. to 85° C., e.g., about 38° C. to 70° C. The insoluble support can be a bead, a matrix, or a planar surface such as a glass slide, membrane, plastic, or a pliable sheet.

In still another aspect, the invention features an insoluble support that includes a first and second plurality of addresses, each address of the first and second plurality having attached thereto an oligonucleotide that has (a) a 5' promoter region that is recognized by a prokaryotic RNA polymerase and (b) a variable 3' target binding region. At each of address of the first plurality, the promoter region of the attached oligonucleotide is recognized by a first RNA polymerase. At each address of the second plurality, the promoter region of the attached oligonucleotide is recognized by a second RNA polymerase.

In one embodiment, the target binding regions of each of the oligonucleotides of the first plurality binds a target site which is on a strand complementary to the target site bound by a target binding region of an oligonucleotide of the second plurality.

The invention also features methods of using the insoluble support, e.g., the SP-TCR method.

The invention also features a kit including a first insoluble support and a second insoluble support. The first insoluble support is an array of SSP oligonucleotides. The second insoluble support is an array of detection probes, each probe querying an allele of a fragment amplifiable by the SSP oligonucleotide array.

In another aspect, the invention features a system that includes: a processor; an array synthesizer; and a repository of polymorphism information. The processor is interfaced with the array synthesizer. The array synthesizer is receives input information that is used to construct an array having 5' anchored SSP oligonucleotides at each address of a plurality of array addresses. The processor can be configured with software to receive a set of polymorphisms for analysis; lookup or compute an appropriate SSP oligonucleotides; and send instructions to the array synthesizer to synthesize an array having primers for the SSAT amplification of the set polymorphisms or an array of detection primers.

The system can further include an array scanner that is also interfaced with the processor. The array scanner can send results from scanning detection arrays to the processor. The results can be stored in a repository of results.

In yet another aspect, the invention features a method that includes: providing an insoluble support having attached oligonucleotides; annealing a sample that comprises RNAs to the insoluble support; extending the attached oligonucleotides using an RNA-directed DNA polymerase to construct DNA replicates of the RNAs; synthesizing DNA strands complementary to the DNA replicates; and transcribing the complementary strand using an RNA polymerase that recognizes the promoter region to produce RNA replicates. Typically, the RNA replicates are anti-sense with respect to the sample RNAs. The sample RNAs can include RNAs, e.g., obtained from a tissue sample such as a mammalian tissue sample. The sample RNAs can be obtained from less than about 1000, 100, or 10 cells. For example, the sample RNAs can be obtained from about 1, 2, 3, or 5 cells. The mRNA can be is less than 10 ng. In one example, the tissue is a normal tissue. In another example, the tissue is tumorous or metastatic.

The method can further include storing the insoluble support for at least 12, 24, 48, 100, or 200 hours prior to the transcribing, e.g., and in some cases at least 6 months, or at least a year.

In one embodiment, the attached oligonucleotides are the same. At least some of the attached oligonucleotides can include a T7 promoter, a homopolymeric T tract, and a terminal A, G, or C. In one embodiment, the attached oligonucleotides are covalently attached to the insoluble support, e.g., by their 5' end. In another, they are non-covalently attached.

The RNA replicates can be labeled. The method can further include hybridizing the labeled RNA replicates to a target, e.g., a filter, a nucleic acid array, or a solution comprising target nucleic acids.

The insoluble support can be a surface of a well of a multiwell plate. The insoluble support can be at least partially composed of glass or a plastic.

In one embodiment, the method further includes hybridizing a labeled probe to the insoluble support.

In another aspect, the invention features a method that includes: providing an insoluble support having attached oligonucleotides; annealing a sample that comprises RNAs to the insoluble support; extending the attached oligonucleotides using an RNA-directed DNA polymerase to construct DNA replicates of the RNAs; synthesizing DNA strands complementary to the DNA replicates; ligating an adaptor to the DNA replicates, and transcribing the complementary strand using an RNA polymerase that recognizes the promoter region to produce RNA replicates. The adaptor can include a promoter region for a second RNA polymerase. The adaptor can further include a unique restriction enzyme recognition site, a translational control sequence, or a sequence encoding a purification tag.

The method can further include reverse transcribing the RNA replicates to form second DNA replicates and transcribing the second DNA replicates using the second RNA polymerase.

In still another aspect, the invention features a method that includes: providing an insoluble support having a 5' attached oligonucleotides; annealing a sample that comprises RNAs to the insoluble support; and extending the attached oligonucleotides using an RNA-directed DNA polymerase to construct DNA replicates of the RNAs. In particular, the invention features an insoluble support made by a method described herein, such as one of the afore-mentioned methods.

The invention also features a kit that includes an array of sense probes and an array of anti-sense probes, wherein for each of at least 10, 20, 30, 40, 60, or 80% of the probes on the array of sense probes, a corresponding and complementary probe is present on the array of anti-sense probes.

In another aspect, the invention features a method that includes: providing a nucleic acid sample; preparing a first and second population of single-stranded nucleic acid strands, wherein the strands of the first population are complementary to the strands of the second population; and evaluating the abundance of a plurality of species in the first population using first probes and the abundance of a plurality of species in the second population using second probes, wherein the first and second probes are substantially complementary. The strands can be RNA or DNA. In one embodiment, the first probes are attached to a first planar array and the second probes are attached to a second planar array. The method can further include determining a score that is a function of the hybridization level of a given sequence to a corresponding first probe and the hybridization level of a complement of the given sequence to a corresponding second probe. For example, the score can be a function of a ratio of the hybridization levels. The method can further include repeating the method for a second sample and comparing the ratio associated with a given sequence between the first and second sample to the ratio associated with a complement of the given sequence between the first and second sample.

In another aspect, the invention features a method that includes: assessing transcript levels using sense copies of a pool of transcripts and anti-sense copies of the pool of transcripts. The method can further include comparing transcript level detected from the sense copies and antisense copies for a plurality of genes. The comparing can include evaluating a ratio between the detected transcript levels for different genes.

The methods described hereiri can produce a population of relevant single stranded nucleic acids. The nucleic acids can, for example, all have the same strandedness. In many embodiments, the product nucleic acid is RNA, which can be enzymatically distinguished from input DNA. Thus, any remnant input DNA can be specifically removed by digestion. Moreover, the methods are particularly suited for multiplex analysis, and, thus, adaptable for applications such as the high-throughput analysis of multiple nucleic acid polymorphisms. The challenges of multiplex analysis are described, for example, in Pastinen et al. ((2000) *Genome Research* 10:1031–1042).

Further, as many embodiments of the invention do not require PCR or another thermal cycling reaction, many and sometimes all steps can be conducted under isothermal conditions, typically at temperatures such as 4° C., 16° C., 25° C., 37° C. or 42° C. Reactions can go for various times, e.g., at least 1, 2, 4, 6, or 12 hours.

Still another advantage is that the methods are readily adapted to amplify DNA rather than RNA. In particular, genomic DNA or cDNA can be analyzed, for example, for polymorphisms. cDNA can be obtained from a single cell, or from a small number of cells (e.g., less than $10^6$, $10^5$, or 1000, 100, or 50 cells).

The invention also provides insoluble supports that are effectively "promoter primer chips." These chips can be produced in quantity and used to query a relevant subset of a genome. Further, as set forth below, once primed with sample nucleic acids or ligated to sample nucleic acids, the chips can be stored, thereby archiving the sample. Later, the stored chips can be used for additional nucleic acid production.

The chips and other insoluble supports also advantageously concentrate relevant target nucleic acids from a complex sample. The removal of non-relevant nucleic acids from a complex sample, before initiating amplification, can further reduce the likelihood of background signals. A background element which appears early in an amplification cycle can dominate species of interest. Some RNA polymerases, such as T7 RNA polymerase, can produce >600 copies of each template in one transcription reaction. Therefore, two to three cycles of transcription-based amplification can achieve very high yields. As exemplified below, the method is highly sensitive. For example, a specific nucleic acid fragment can be amplified from 100 ng of human genomic DNA or from a cDNA, e.g., from a single cell.

A further advantage is that the method enables the production and archiving of a reproducible nucleic acid library without the use of cells. The library can be stored, e.g., as an immobilized population of nucleic acids. Because the nucleic acids are not introduced into cells, representation of nucleic acids in the library is not subjected to biases that can be caused by cellular toxicity and other unpredictable factors.

In addition, as described for some methods, use of an insoluble support (such as a pin or an array) enables simple exchange of reaction solutions. For example, enzymes can be removed without complex steps such as heat inactivation, phenol extraction, or ethanol precipitation.

With respect to many embodiments, it is also found that transcription-based amplification can include designing the promoter position to create a defined terminus for each RNA product. Probes for each product are similarly designed.

An oligonucleotide refers to a nucleic acid of less than 150 nucleotides. Oligonucleotides can be produced synthetically or enzymatically (e.g., by excision from a larger nucleic acid). An oligonucleotide can include a double-stranded region, e.g., by self-annealing or by annealing to another nucleic acid. An oligonucleotide is typically a DNA molecule, e.g., with an extendable 3' end. An oligonucleotide can include one or more modification (e.g., attached ligands).

The details of a number of embodiments of the invention are set forth in the accompanying drawings and the description below. Other features, objects, and advantages of the invention will be apparent from the description and drawings, and from the claims.

DETAILED DESCRIPTION

Figure 1:
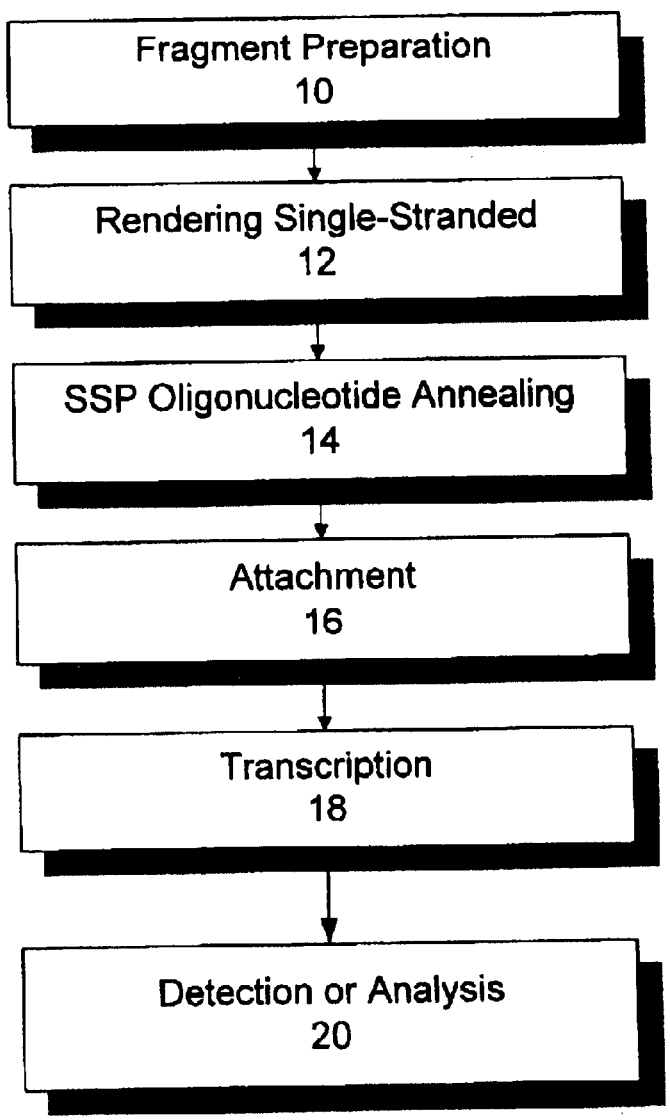
FIG. 1 is a flow chart of the steps in an exemplary SSAT method.

One exemplary application enables the amplification of nucleic acid populations (e.g., mRNA or DNA populations) by transcription using immobilized template nucleic acids. An exemplary process is as follows:

First, an insoluble support is provided. The insoluble support has immobilized oligonucleotides that include a promoter sequence and a target annealing sequence. The 3' terminus is available for extension by a polymerase. The 5' terminus of the promoter sequence is spaced from the insoluble support by a distance of at least 4 nm. See below "Spacer Lengths". A linker sequence can be present between the promoter sequence and the target annealing sequence. The linker sequence can include, for example, one or more of a restriction site (e.g., a 4-, 6- or an 8-base cutter such as AscI), a sequence encoding a purification tag (such as the hexa-His tag or S-tag), a splicing sequence, and a translational control signal (such as the Kozak consensus sequence or other ribosome entry site) or complements thereof.

For an embodiment in which mRNA is amplified, for example, the target annealing sequence can include poly-dT. In some embodiments, the target annealing sequence includes a single A, G, or C nucleotide at its 3' terminus. The A, G, or C nucleotide serves to anchor the poly-dT primer at the 5' end of the poly-A tract of mRNA. Typically, the insoluble support includes a population of immobilized oligonucleotides with different terminal nucleotides, e.g., so that all mRNAs can hybridize to the target annealing sequence. Dinucleotide anchors can also be used, as can gene or family specific primers. Other target annealing sequences can also be sued (e.g., target specific nucleic acid sequences or repetitive sequences, e.g., as for some genome nucleic acid sequences)

The insoluble support is then washed and equilibrated in 1× first strand synthesis buffer (e.g., 1× first strand synthesis buffer (S0mM Tris-HCL, pH 8.3 at 42° C.; 50 mM KCl; 10 mM MgCl$_2$; 0.5 mM spermnidine; 10 mM DTT). The mRNA sample is annealed to the immobilized oligonucleotides in the presence of first strand synthesis buffer (e.g., including DNase inhibitor). The annealing can proceed at 42° C. for at least 5 minutes.

After annealing, cDNA synthesis is initiated by the addition of sodium pyrophosphate, AMV reverse transcriptase (e.g., from Universal Riboclone cDNA Synthesis System Catalog No. C4360 from Promega Corp, Madison, Wis., USA) and deoxynucleotides (e.g., 1 mM each of dATP, dCTP, dGTP, dTTP). The reaction can proceed, e.g., at 42° C. for at least 30 minutes.

After synthesis of the first cDNA strand, the insoluble support now has attached cDNA copies of each annealed mRNA. The cDNA copies are immobilized and are operably linked to a promoter since they are constructed by extension of the immobilized oligonucleotide. Thus, the insoluble support can be stored at this stage, and then retrieved for later amplification and analysis.

A variety of methods can be used to produce the second cDNA strand, if required. See below ("Second Stand Synthesis"). The insoluble support can be stored at this point. Typically, the insoluble support is washed extensively and incubated in a cryoprotectant (e.g., 10% glycerol) prior to storage.

After second cDNA strand synthesis, in some embodiments, a DNA adaptor is ligated to the free terminus of the immobilized cDNA. The DNA adaptor can include a transcription promoter, e.g., the T3 DNA polymerase promoter. This design is useful for the transcription chain reaction described herein. The adaptor can also include one or more of a restriction site (e.g., a 4-, 6- or an 8-base cutter such as AscI), a sequence encoding a purification tag (such as the hexa-His tag or S-tag), a splicing sequence, and a translational control signal (such as the Kozak consensus sequence or other ribosome entry site) or complements thereof.

The support can be used to generate RNA copies of the original sample. The support is first equilibrated in RNA polymerase transcription buffer and then contacted with RNA polymerase transcription reagents, e.g., T7 RNA polymerase and ribonucleotides (e.g., as provided by AMPLISCRIBE™ T7 High Yield Transcription Kit, Catalog No. AS2607, Epicentre, Madison, Wis.). Reactions are appropriately incubated, e.g., at 37° C. for at least one hour. After incubation, amplified mRNA can be harvested from the reaction solution.

For transcription chain reaction embodiments, the amplified mRNA can be amplified using the other promoter (e.g., the T3 DNA polymerase promoter) as described above.

The insoluble support serves as a DNA archive of the original mRNA sample. The archive can be returned to, time and again. Moreover, the archive is amplified by transcription, which restores the original sample in its RNA state. Such amplification is also linear and may be less susceptible to biasing events than, e.g., exponential amplification. In some embodiments, the method is supported by a single primer for reverse transcription. The primer is universal for all polyadenylated mRNAs.

Spacer Lengths

We have discovered that nucleic acid amplification according to the methods described herein is remarkably improved by spacing the promoter sequence from the insoluble support. The distance between the 5' terminus of the promoter and the support is at least 4 nm, and is described with additional particularity as follows and by Examples 1–4, below:

1) Non-Covalent Immobilization:

Immobilization oligonucleotides can be inmnobilized by non-covalent interaction between a ligand that is covalently attached to the oligonucleotide and a protein immobilized on the support. For example, the ligand can be biotin and the interaction can be between biotin and a biotin-interacting protein (e.g., streptavidin or avidin). When this configuration (ligand/ligand-binding protein, e.g., biotin/biotin-interacting protein) is used to immobilize the oligonucleotide to the insoluble support, optimal spacings between the immobilized nucleotide position (e.g., the 5' nucleotide) and the 5' end of the promoter sequence is at least 5 nucleotides, e.g., between 6 and 20 nucleotides, or between 6 and 15, or 6 and 12 nucleotides, e.g., 6, 7, 8, 9, 10, 11, or 12 nucleotides. In one embodiment, it is also possible to substitute the nucleic acid spacer sequence with a non-nucleic acid spacer, e.g., a chemical linker described below.

Other examples ligand/ligand-binding protein interactions include: FK506 and FK506BP, chitin and chitin binding protein; cellulose and Cellulase (CBD); amylose or maltose and maltose binding protein; methotrexate and dihydrofolate reductases.

2) Covalent Immobilization

Oligonucleotides can be immobilized by covalent coupling chemistries, e.g., by a homopolymeric linker (e.g., a polyethylene glycol linker), and phosphate linkages. Additional examples of homopolymeric linkers include: polymers with subunits having 2, 3, or 4 main chain atoms, and between 5 and 12 repeats of the subunits. For example, the linker can be composed of polyethylene glycol (($CH_2CH_2O$)$_n$–, e.g., where n is >8, e.g., 8 to 20, 8 to 16 or 8 to 12) and/or polymethylene, (($CH_2$)$_n$–, e.g., where n is >18, e.g., 18 to 60, or 24 to 48). Generally it is possible to use any chemical linker (e.g., without nucleotide units) that has the same physical length or atom length as a linker described herein, e.g., a homopolymeric linker described above, e.g., including 18 to 60, or 24 to 48 main chain atoms.

An oligonucleotide that includes a nucleotide that is directly coupled to the immobilized support can include a spacer of between 15 and 45 nucleotides, e.g., between 20 and 35 nucleotides, e.g., between 23 and 28 nucleotides, or about 25 nucleotides. The oligonucleotide can be coupled, e.g., using carbodiimide activation.

Figure 12:
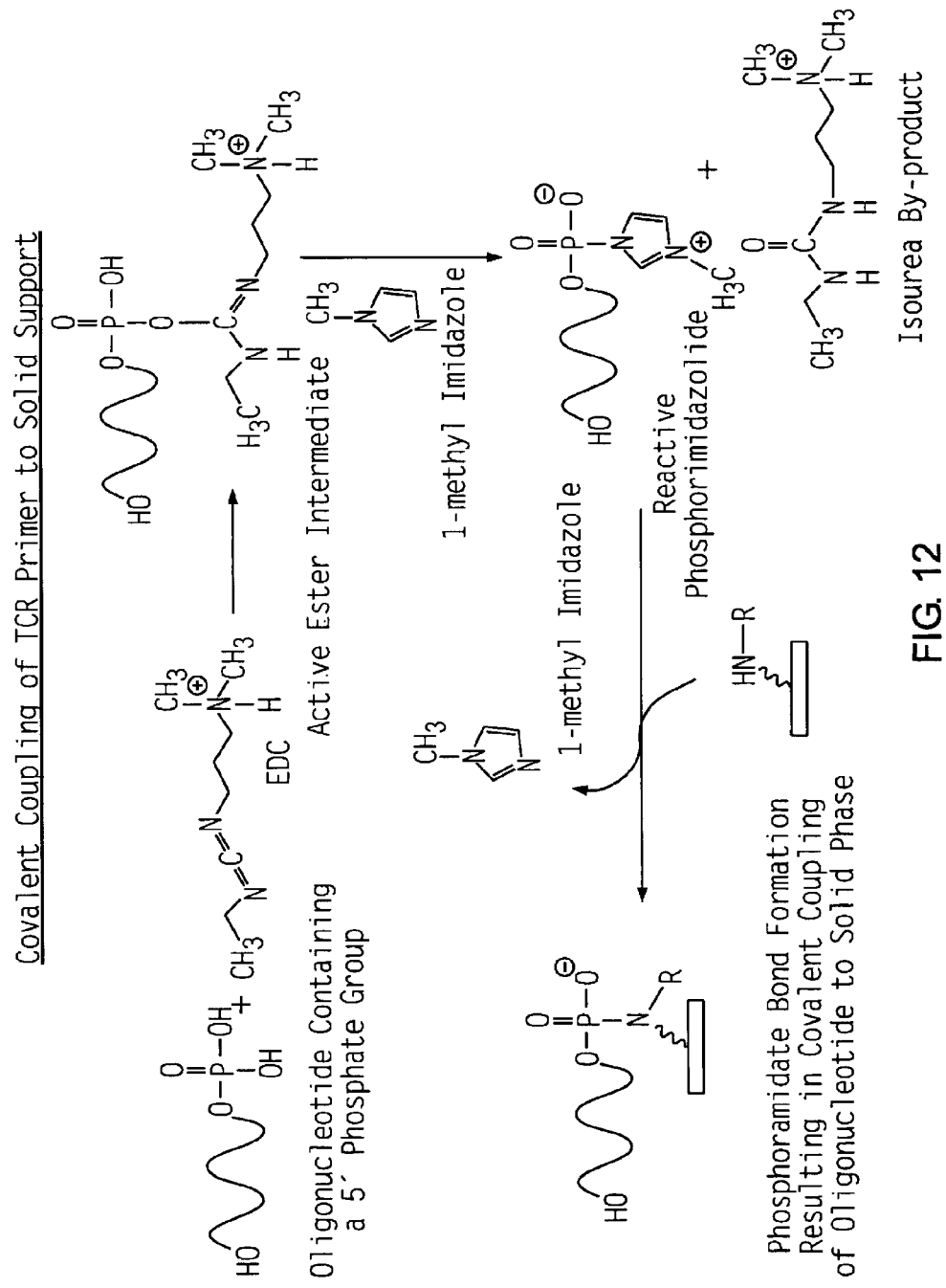
FIG. 12 is an exemplary method for covalently coupling an oligonucleotide to an insoluble support.

In one embodiment that uses carboduimide activation, a primer oligonucleotide containing a 5'-phosphate group is activated with ethyl 1,1-dimethylaminopropylcarbodiimide hydrochloride (EDC) in the presence of 1-methylimidazole. See, e.g., Chu et at. (Nucleic Res., 11,6513 (1983). The active phosphate ester intermediate is converted into a reactive phosphorimidazolide which reacts spontaneously with an amino group on the insoluble support. This covalent coupling chemistry further ensures that only the 5'-end of the primer oligonucleotide is attached to the insoluble support. See, e.g., FIG. 12.

Other attachment chemistries include: coupling between an amine-including oligonucleotide and an activated carboxylate group or succinimidyl ester; coupling between a thiol-including oligonucleotide (SH-oligo) and an alkylating reagent such as an iodoacetamide or maleimide; coupling of an Acrydite-oligonucleotide through a thioether. See, e.g., Adessi et al. (2000) *Nucleic Acids Research* 28:e87; Ghosh, and Musso (1987) *Nucleic Acids Res.* 15:5353–5372; Lindroos et al. (2001) *Nucleic Acids Res.* 29:e69; Rogers et al. (1999) *Anal. Biochem.* 266:23–30.

Nucleotide regions of spacers can be prepared using any nucleic acid sequence, for example, a homopolymeric sequence, a low complexity sequence, a medium complexity sequence, a complex sequence, or a sequence absent from the sample of relevance. A "low complexity sequence" is a sequence that includes repeating units of 4, 3, or 2 nucleotides. A "medium complexity sequence" includes fewer than three types of repeats, each repeat being 2, 3, 4, or 5 nucleotides. A sequence absent from a sample of relevance can be identified by searching a computer database of sequences potentially in the sample. For example, if the sample is human, it is possible to identify a spacer that is not present in human genome sequence or that is not complementary to any human genome sequence.

Second Strand Synthesis

One method includes reaction with a stranddisplacing DNA polymerase (e.g., DNA polymerase I) and RNase H, e.g., at 16° C. RNase H is used to nick the RNA strand. If necessary, the reaction can be completed by T4 DNA polymerase. The second cDNA strand forms homoduplexes of DNA on the array and thereby contributes to stability.

Figure 14:
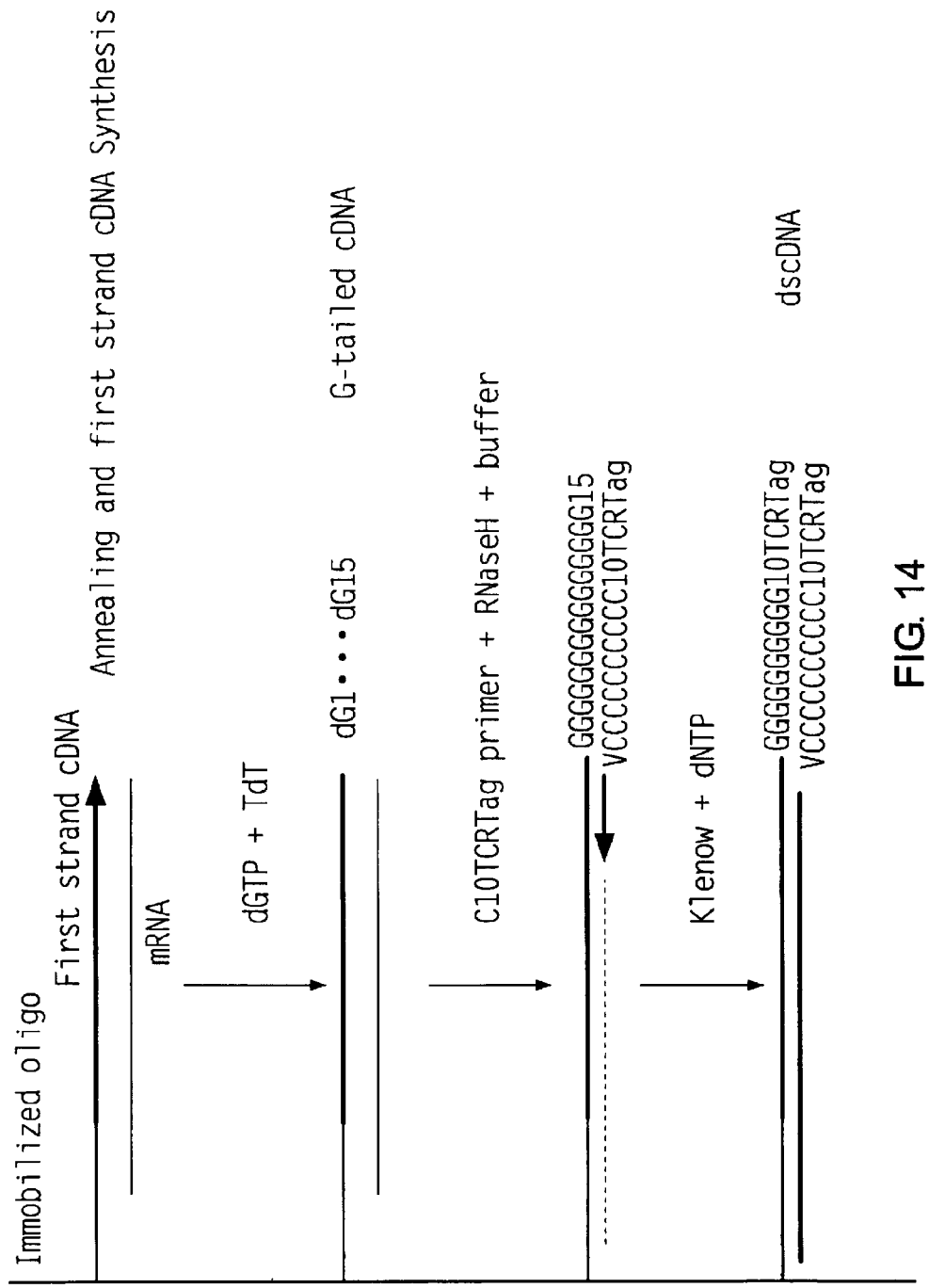
FIG. 14 is an exemplary method for synthesizing a second DNA strand.

Another method includes tailing of the extended immobilized oligonucleotide by terminal transferase, e.g., in the presence of dGTP so that a polyG tail is add, e.g., about 10–20, 12–18, or an average of 15 nucleotides in length. After the tailing, a primer that includes C is annealed, and optionally ligated, and extended. See FIG. 14. See generally, e.g., Okayama and Berg *Mol. Cell. Bio.* 2:161–170, 1982; Spickofsky and Margolskee *Nucleic Acids Res.* 19: 7105–7111, 1991); Dugaiczyk, et. al. *Biochemistry* 19:5869–5873, 1980).

It is also possible for a hairpin to form spontaneously such that the terminal nucleotide can be extended to form the complementary strand.

Still another method uses primer corresponding to the 5' end of the target sequence, e.g., complementary to the 3' end of the extended oligonucleotide. Random hexanucleotides or other priming sequences can also be used, particularly after removal of the RNA strand, e.g., by denaturation or nicking with RNase H.

SSP Oligonucleotide Design

SSP oligonucleotides are used to attach a promoter for an RNA polymerase to a DNA template. The SSP oligonucleotides used in this method generally have a length of 25 to 100 nucleotides, e.g., about 30 to 50 or 40 to 60 nucleotides. The SSP oligonucleotides are also designed so that the promoter sequence is spaced from the insoluble support when the SSP oligonucleotide is immobilized. The spacing can be as described above.

An SSP oligonucleotide has a 3' sequence, also termed "target binding region," which anneals to a target site within a target fragment. This sequence can be substantially homologous, e.g., 90 to 100% identical, to the target site. An identical or nearly identical sequence increases specificity of amplification. The length of the target binding region can be selected such that the $T_m$ for a duplex formed between it and the target site is at least about 42° C., 50° C., or 55° C. The target binding region can be optimized such that it does not anneal to itself or the remainder of the SSP oligonucleotide (e.g., form hairpins).

An SSP oligonucleotide also contains a promoter sequence 5' end to the target sequence. The promoter sequence is recognized by an RNA polymerase. The RNA polymerase can be prokaryotic, eukaryotic, or archeal. For example, the RNA polymerase can be a prokaryotic bacteriophage RNA polymerase such as the T7, T3, and SP6 RNA polymerases. Hence, exemplary promoter sequences include, but not limited to, T7, T3, Sp6 RNA polymerase promoters sequences. Generally, any RNA polymerase that can be specifically directed to a promoter can be used. For example, SP01 promoters can be used in conjunction with sigma factors from the *Bacillus subtilis* phage SP01 to target RNA polymerase to SP01 promoters.

The SSP oligonucleotide can be attached or attachable to an insoluble support. For example, the SSP oligonucleotide can also include a modification to facilitate affinity capture of the target or of the duplex formed by extension of the target-SSP oligonucleotide complex. The modification can include, for example, a small molecule of less than 1000 Daltons molecular weight for binding by a protein that binds (e.g., specifically binds) to the small molecule. For example, one or more biotinylated deoxynucleotides (or other ligands) can be used. Other useful modifications include amino and thiol moieties. A biotinylated moiety can be bound to immobilized streptavidin or avidin. Other useful non-covalent and covalent linkages are widely known. For some reactions, e.g., using a biotinylated SSP oligonucleotide, about 0.1, 1, 5, 10, 20, or 100 pmol of SSP oligonucleotide are used per reaction. The reaction might be about the size of a well of a 96-well carrier.

In one embodiment, the primer includes a sequence have one strand of a restriction enzyme recognition site. The primer can also include a modified base, such as α S-dNTP, within the recognition site, e.g., such that the primer strand is not cleaved. DNA polymerase will then recognize the nick, and start polymerization which results in displacement of the nicked DNA strand. Repeat nicking and polymerization lead to linear amplification of one strand of the target DNA.

Optionally, a linker sequence can be included between the SSP oligonucleotide promoter sequence and the target sequence. The linker sequence is transcribed, and can include restriction endonuclease sites (e.g., sites for a 6- or 8-base pair cutter) to facilitate cloning of the amplified nucleic acids, a synthetic identification tag, or a universal sequence. The linker region can include a sequence that is recognized by an RNA binding protein when the linker region is transcribed into RNA. Exemplary RNA binding proteins include Tat and Nus.

In one embodiment, the linker region includes an internal ribosome entry site, an initiator methionine, an epitope tag, a purification or detection tag, and/or a translational regulatory sequence.

Further exemplary methods of SSP oligonucleotide design are also described in "Ligation" and "Software," see below.

Once designed SSP oligonucleotides can be synthesized using standard oligonucleotide synthesis chemistry. Further, if a clone bank is generated, SSP oligonucleotides can be produced enzymatically (e.g., by PCR) or by isolation from a host cell (e.g., *E. coli*).

SSP Oligonucleotide Annealing

The SSP oligonucleotides are annealed to single stranded DNA from the exonuclease treatment. The annealing can be performed at a temperature below the $T_m$ of the SSP oligonucleotide for its target binding site. Hybridization of SSP oligonucleotides to the single stranded target fragments can be performed in any container, e.g., a tube, such as a micro-centrifluge tube, a well, or a flow cell. The SSP oligonucleotide can be attached to an insoluble support, either before, during, or after annealing.

A variety of hybridization conditions can be used. Hybridization conditions are described, for example, in standard laboratory manuals such as (Molecular Cloning, $3^{rd}$ edition, Cold Spring Harbor Press, ed. Sambrook & Russell). Temperature and salt concentration can be selected to achieve the desired stringency.

Figure 3:
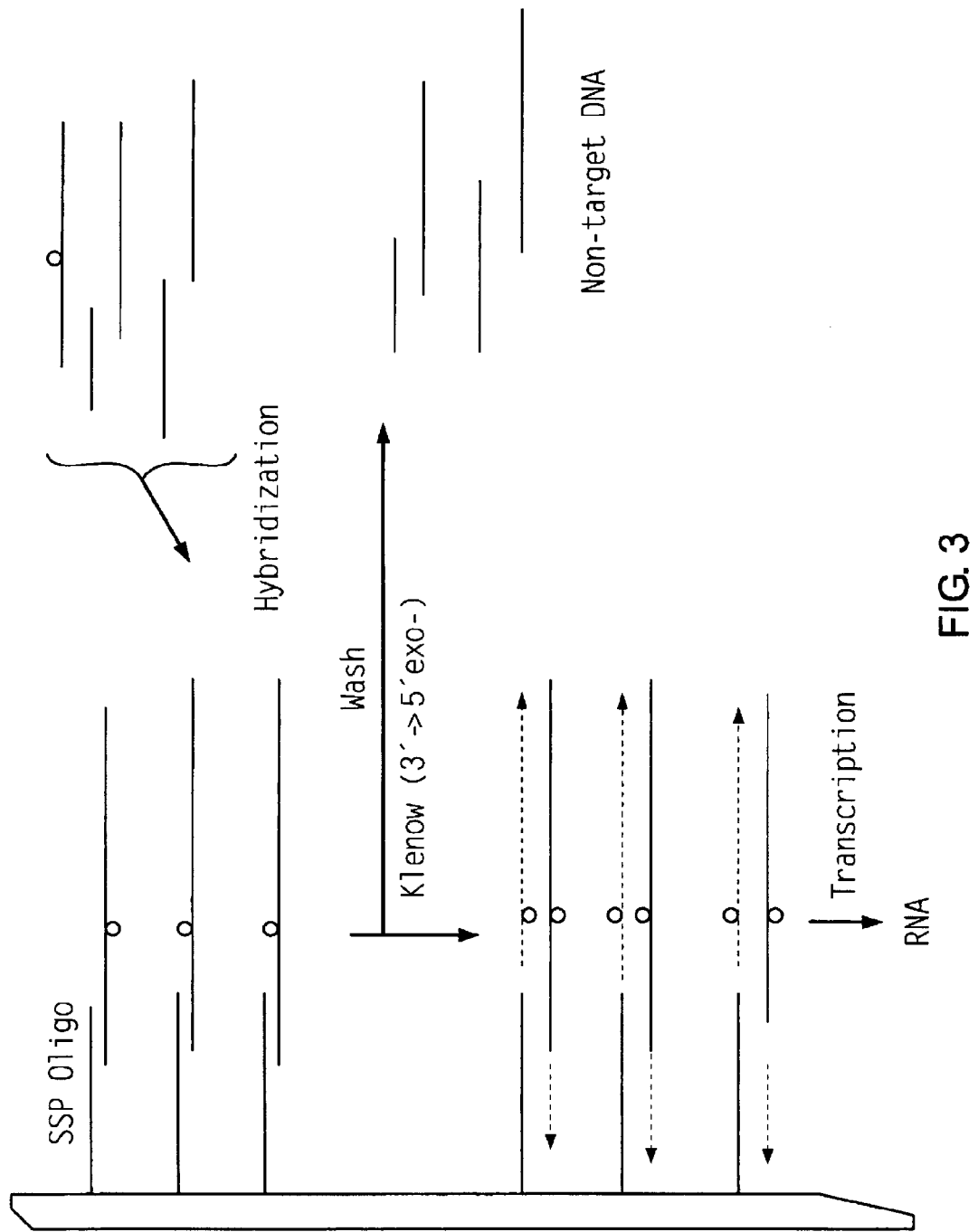
FIG. 3 is a schematic of an implementation of the SSAT method for a complex input sample and target specific SSP oligonucleotides.

One method is to hybridize the single-stranded targets to 5'→3' directionally anchored SSP oligonucleotides as is illustrated in FIG. 3. After hybridization, unbound DNA can be removed by washing with buffers.

Template Extension

DNA polymerase is used to append the SSP oligonucleotide to the target sequence by primer extension, thereby forming double-stranded DNA. Exemplary DNA polymerases include the Kienow fragment (3'-5' exo), and SEQUENASE™ 2.0 (Amersham Pharmacia Biotech). Any DNA polymerase may suffice, particularly those lacking 3' to 5' exonuclease activity. Conditions for double-stranded DNA synthesis are described, for example, in Gubler (1987) *Methods Enzymol* 152: 330–335.

The DNA polymerase can extend the annealed target nucleic acid segment using the promoter (or other non-target binding region) of the SSP oligonucleotide as a template. This step renders the promoter region double-stranded and functional. Further the extension process "operably links" the promoter to the target fragment. As used herein, the term "operably linked" refers to a functional linkage between the affecting sequence (typically a promoter) and the controlled sequence.

Since a double stranded region is optional in the region after the +1 site of the promoter, at least for the bacteriophage RNA polymerases such as SP6, T7, and T3, in some embodiments the 3' terminals of the SSP oligonucleotide can be blocked. In these implementations only the promoter region is rendered double-stranded. The SSP oligonucleotide is not used as a primer, but as a template.

In other embodiments, the SSP oligonucleotide is also extended. This implementation is useful as it renders both the promoter and the target double stranded. The extended nucleic acids can be stored as DNA duplexes. Such stored nucleic acid has the advantage of conformational and chemical stability.

Ligation

Figure 9:
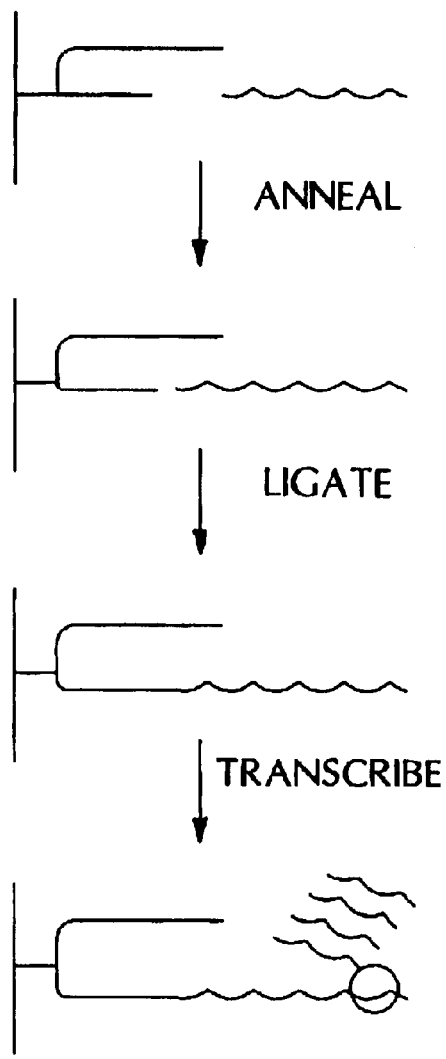
FIG. 9 is a schematic of an example of attachment by ligation.

In another embodiment, depicted in FIG. 9, the target fragment is ligated to the bottom strand of an SSP duplex, which includes both the SSP oligonucleotide, and a complementary strand. The three component strands can be added in any order. Since the template for transcription can be single stranded (see below), so long as the promoter is double-stranded, the asymmetric hybrid formed by the three component strands is sufficient for transcriptional amplification. Two components can also be used, for example, if the SSP duplex is formed from a hairpin nucleic acid that includes the SSP oligonucleotide sequences and the complementary region.

Amplification by Transcription

The T7 polymerase polypeptide can be isolated from the cloned gene, the T7 gene 1, see e.g., U.S. Pat. No. 5,869,320 (Studier et al.). T7 RNA polymerase can be purified from induced cells that have a nucleic acid for T7 gene operably linked to an inducible promoter. Chamberlin et al., (1970) *Nature,* 228, 227–231 describes one exemplary scheme for purifying the polymerase.

T7 RNA polymerase is highly specificity for its promoter site (Chamberlin et al., in *The Enzymes,* ed. P. Boyer (Academic Press, New York) pp. 87–108 (1982)). The T7 polymerase recognizes a highly conserved sequence spanning about bp−17 to about +6 relative to the start of the RNA chain (Dunn and Studier, (1983) *J. Mol. Biol.* 166: 477–535 and (1984) *J. Mol. Biol.* 175: 111–112. The essential region of the promoter extends from −17 to +1. Moreover, the only region of the template strand that must be double-stranded DNA is this region. The remainder of the template can be single-stranded.

T7 RNA polymerase is particularly useful for amplification of diverse nucleic acid sequences as a result of the dearth of efficient termination signals for T7 RNA polymerase (see, Rosenberg et al., (1987) *Gene* 56: 125–135. The T7 RNA polymerase is available, e.g., from Promega Biotech, (Madison, Wis.) and Epicentre Technologies, (Madison, Wis.).

SP6 and T3 RNA polymerases have similar properties. Further, each of these three polymerases is highly specific as it does not transcribe non-cognate promoters. The minimal efficient promoter sequences for these polymerases are listed in Table 1 below. The +1 nucleotide is underscored. Other prokaryotic promoters can be used, e.g., a promoter recognized by an *E. coli* RNA polymerase. The 5' end of a promoter can be defined, e.g., by mutational analysis (e.g., deletion mapping), wherein the 5' end bounds the minimal region that is sufficient to provide at least 70% of the wildtype promoter's activity.

TABLE 1

Bacteriophage RNA Polymerase Promoters

| RNA polymerase | Specific Promoter Sequence |
| --- | --- |
| T7 | TAATACGACTCACTATAGG (SEQ ID NO:23) |
| T3 | AATTAACCCTCACTAAAGG (SEQ ID NO:24) |
| SP6 | ATTTAGGTGACACTATAGA (SEQ ID NO:25) |

To obtain amplified RNA, RNA polymerase reaction buffer, excess of all four ribonucleotides, and the corresponding RNA polymerase enzyme are added, and incubate at 37° C. for 2–24 hours. In vitro transcription is described, e.g., in Melton, D. et al. (1984) *Nucl. Acid. Res.* 12:7035. The transcription reaction buffer can include a variety of components, e.g., including:

1 to 20 mM NaCl 24, 34, or 40 mM $Mg_2Cl_2$ 10 to 50 mM Tris·HCl (pH about 7.3, 7.4, or 7.5)

1, 2, 3, 5, 7.5, 10 mM rNTP 1,3,5, 10 mM DTT

2 U/μl Superaseinhibitor

To obtain labeled RNA to be used as hybridization probe in sequence analysis, one or more labeled ribonucleotides are also added. Depending on the intended detection method, the labels can be, but not limit to, fluorescent dyes such as fluorescein and the cyanine dyes (Cy3, Cy5, Alexa 542, and Bodipy 630/650); radiolabels such as $^{32}P$, $^{33}P$, $^{35}S$, and $^{3}H$; colorimetric or chemiluminescence; and binding pair components such as biotin or digoxygenin.

Post Processing, Archiving, and Storaye

The method can further include any of a number of post-processing steps. For example, the RNA products can be reverse transcribed into DNA using specific or random primers. Clearly, the RNA products can be used for a variety of purposes. For example, the RNA products (if they have the appropriate strandedness) can be translated, and the translation products analyzed, e.g., for an activity or by contacting the translation products with an antibody. Translation products can be analyzed, e.g., to evaluate one, two, three or more criteria about each product, e.g., using gel electrophoresis, 2D gel electrophoresis, mass spectrometry, and other methods. The information can be stored in a database, e.g., using a record that includes two, three or more fields, e.g., to provide a multidimensional vector.

The RNA can be quantitated, e.g., to determine the abundance of different species. If the RNA is labeled, it can be hybridized to an array of positional probes for the different known RNA species. In some cases, the RNA is itself functional, e.g., the RNA is an aptamer or a catalyst. Such RNA can be analyzed for binding or catalytic properties.

Anchored, promoter appended DNA target can also be reused and/or stored for future reference. For example, if a chip of SSP oligonucleotides is used, the chip can washed free of reagents. The washed chip can either be immediately reused for additional rounds of transcriptional amplification or stored, e.g., in an archival process. A stored chip can be dehydrated and frozen, or coated with a cryoprotectant such as a glycerol solution, and frozen. When desired, a stored chip can be retrieved, washed, and applied with fresh reagents for transcription, e.g., ribonucleotides and the appropriate RNA polymerase. As described below, a variety of insoluble supports (e.g., pins, microtitre wells, spin cups, matrices, and membranes) can be used.

Likewise, with respect to the cyclic TCR method, in which two different sets of templates (e.g., T7 and T3) are produced, the templates may be archived separately or together.

By coupling templates from different cycles to separate supports, a master and working set of templates can be generated. The working sets can be distributed to different users (e.g., customers). The master set can be used to produce additional working sets and may also be stored for reference or quality control.

Transcription Chain Reaction (TCR)

Figure 6:
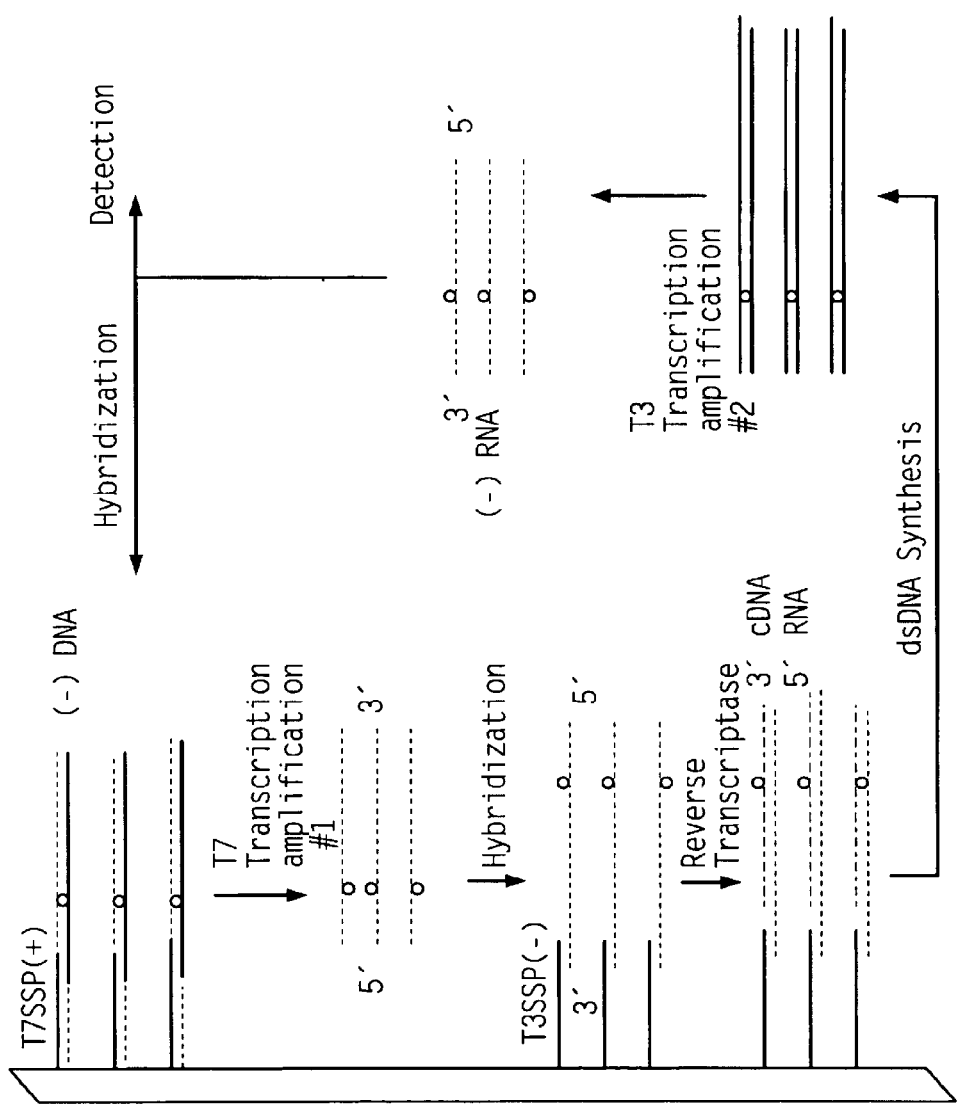
FIG. 6 is a schematic of an example of dual promoter SP-TCR method.

Turning now to FIG. 6, increased amplification is achieved by using the RNA products as templates for additional transcription. The RNA products are converted to DNA by reverse transcription in a format analogous to the process described above for SSP oligonucleotide directed synthesis. The RNA transcripts made from the SSP oligonucleotide appended double stranded DNA, denoted as (+) target strand, are captured by a second SSP oligonucleotide which contains a sequence complementary to the newly synthesized RNA strand, e.g., at the 3' end of the RNA strand. The promoter segment of the second SSP oligonucleotide can be different from the promoter of the first SSP oligonucleotide. The captured (+) RNA can now be converted to double-stranded DNA by reverse transcriptase and DNA polymerase.

Transcription from these newly synthesized DNA produces RNA corresponding to the (−) strands of the target, and results in enhanced amplification. The method can be used to detect sequences at very low concentrations, e.g., from a single cancer cell in a population of normal cells.

As described above, as the nucleic acid promoter-target fusions are captured, the insoluble support attached to the first and second SSP oligonucleotides can be stored for later rounds of transcription.

In one embodiment, the insoluble support contains multiple pairs of first and second SSP oligonucleotides, e.g., to amplify multiple different targets.

Figure 7:
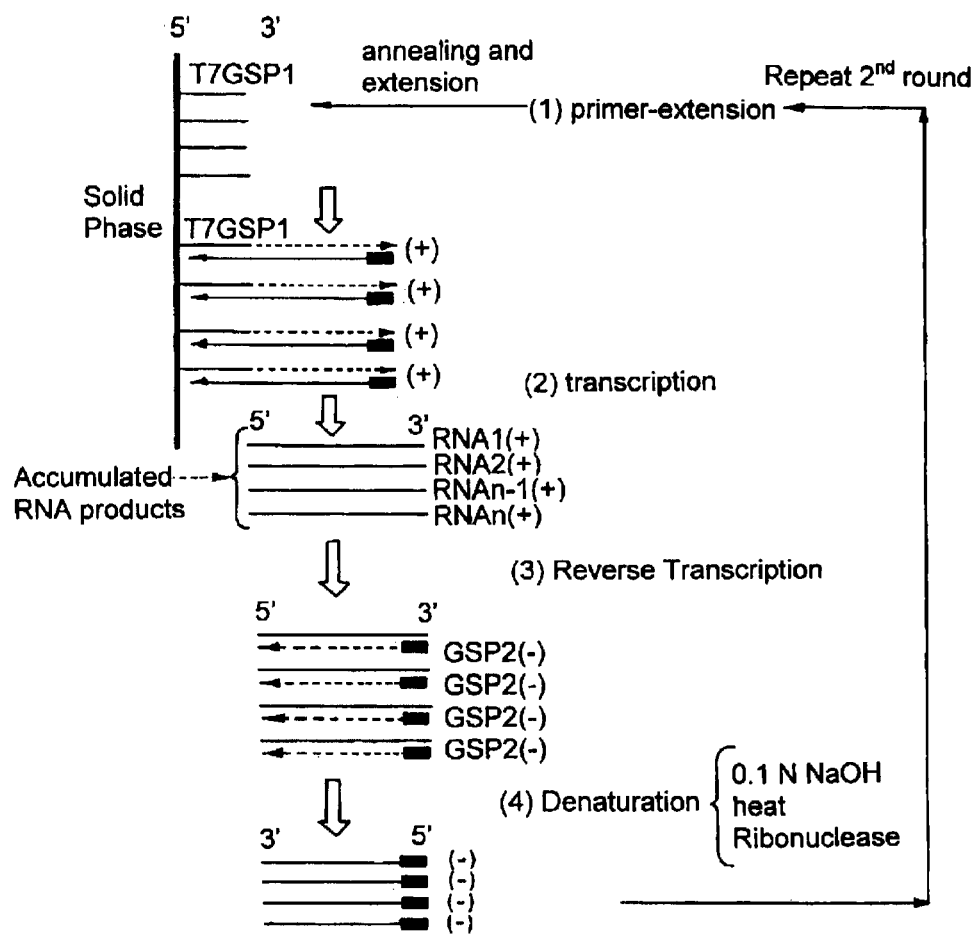
FIG. 7 is a schematic of an example of single promoter SP-TCR method.

Referring to FIG. 7, RNA products from an initial amplification stage are reverse transcribed, e.g., using a target specific primer. The DNA strand from reverse transcription can be rendered single stranded, e.g., by mild alkali hydrolysis, heat treatment, 50% formamide at 50° C., or ribonuclease digestion, e.g., using RNaseH. The single stranded DNA replicates can then anneal to the available immobilized SSP oligonucleotides. The process allows for enhanced amplification.

Figure 8:
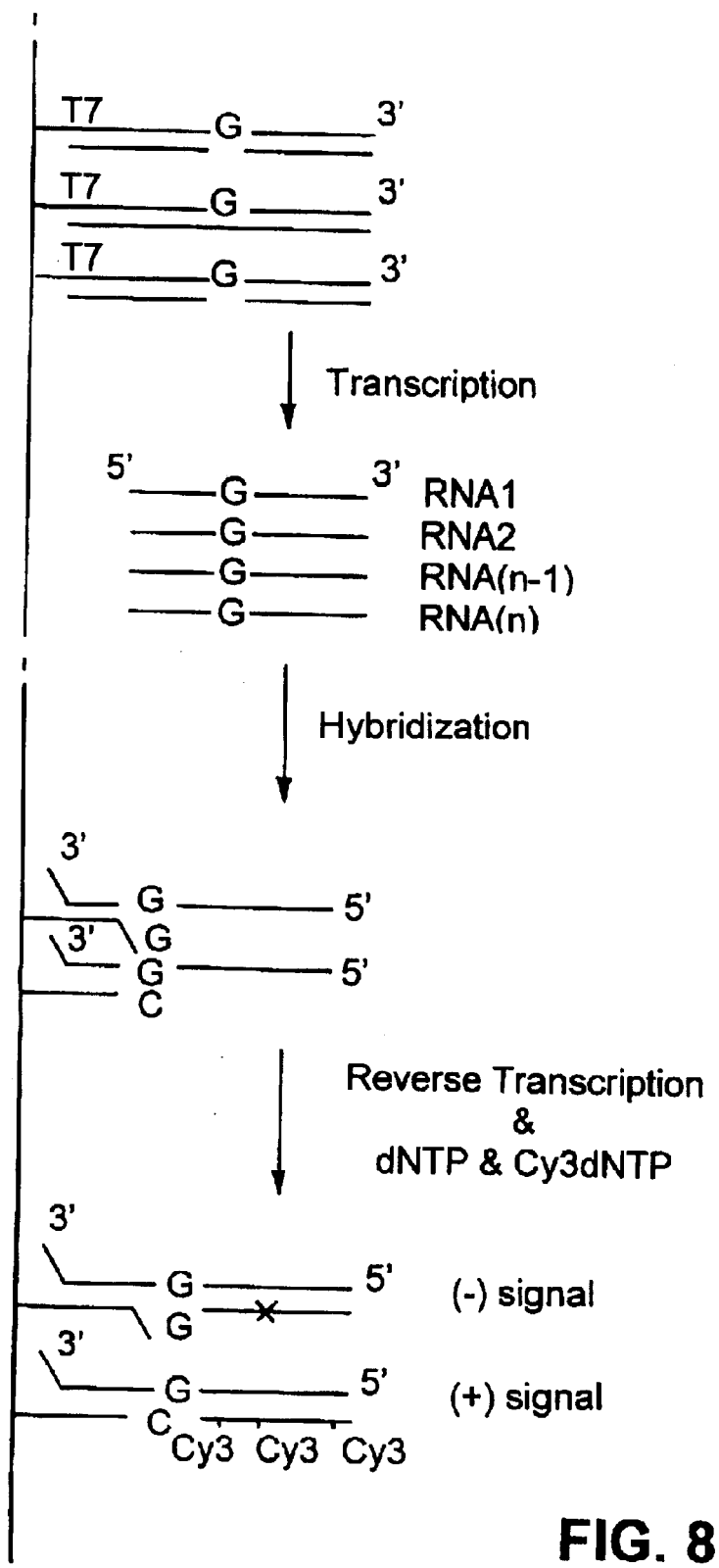
FIG. 8 is an example of SNP detection method.

Referring to FIG. 8, a fragment containing a single nucleotide polymorphism at a query site is amplified using the SSAT method. Then, RNA products are hybridized to immobilized reverse transcription primers. The reverse transcription primers position their ultimate 3' nucleotide opposite the query site. Reverse transcription only proceeds if the ultimate 3' nucleotide is complementary to the query site nucleotide. The incorporation of label, e.g., a Cy3 labeled dNTP can be used to monitor the process.

Figure 10:
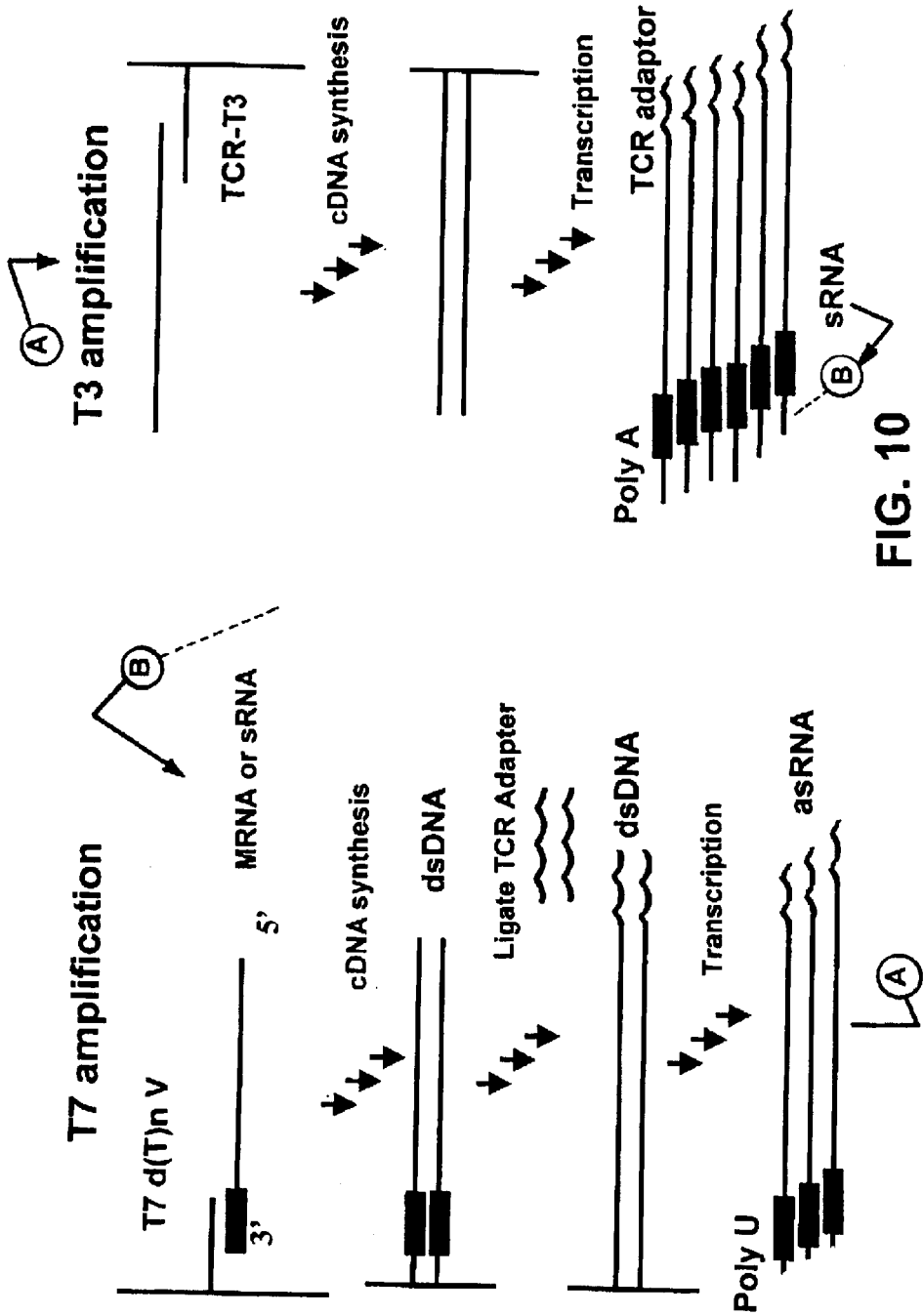
FIG. 10 is a schematic of an example of cycles of TCR.

Referring to FIG. 10, cycles of T7 (left) and T3 (right) amplification are shown. mRNA or sRNA (from a cycle of T3 amplification) are hybridized to SSP oligonucleotides (e.g., T7-d(T)nV) that are attached to support. The SSP oligonucleotide can include a spacer sequence between the promoter and the insoluble support attachment site. For example, the spacer can be at least 6, 12, 18, or 24 nucleotides in length. Template DNA is produced, e.g., by cDNA synthesis. An adaptor molecule is ligated to the template in an initial cycle (e.g., this is optional if sRNA is used). The adaptor preferably includes a tag sequence that is absent from the sample. A computer program can be used to predict sequences that should be absent from a sample obtained from a particular organism, e.g., by comparison to a comprehensive database of genomic or cDNA sequences from that organism. After ligation of the adaptor, transcripts (aRNA) are produced using T7 polymerase.

The transcripts include the tag sequence as well as the sequence from the sample nucleic acid. Transcripts are then hybridized to a T3-TCR SSP oligonucleotide attached to the same support or another insoluble support (see circled A flowchart indicator). Again, cDNA is produced from the annealed transcripts. The T3 polymerase is now used to produce sRNA. The sRNA can be cyclic deployed to produce additional aRNA transcripts (see circled B flowchart indicator).

Figure 11:
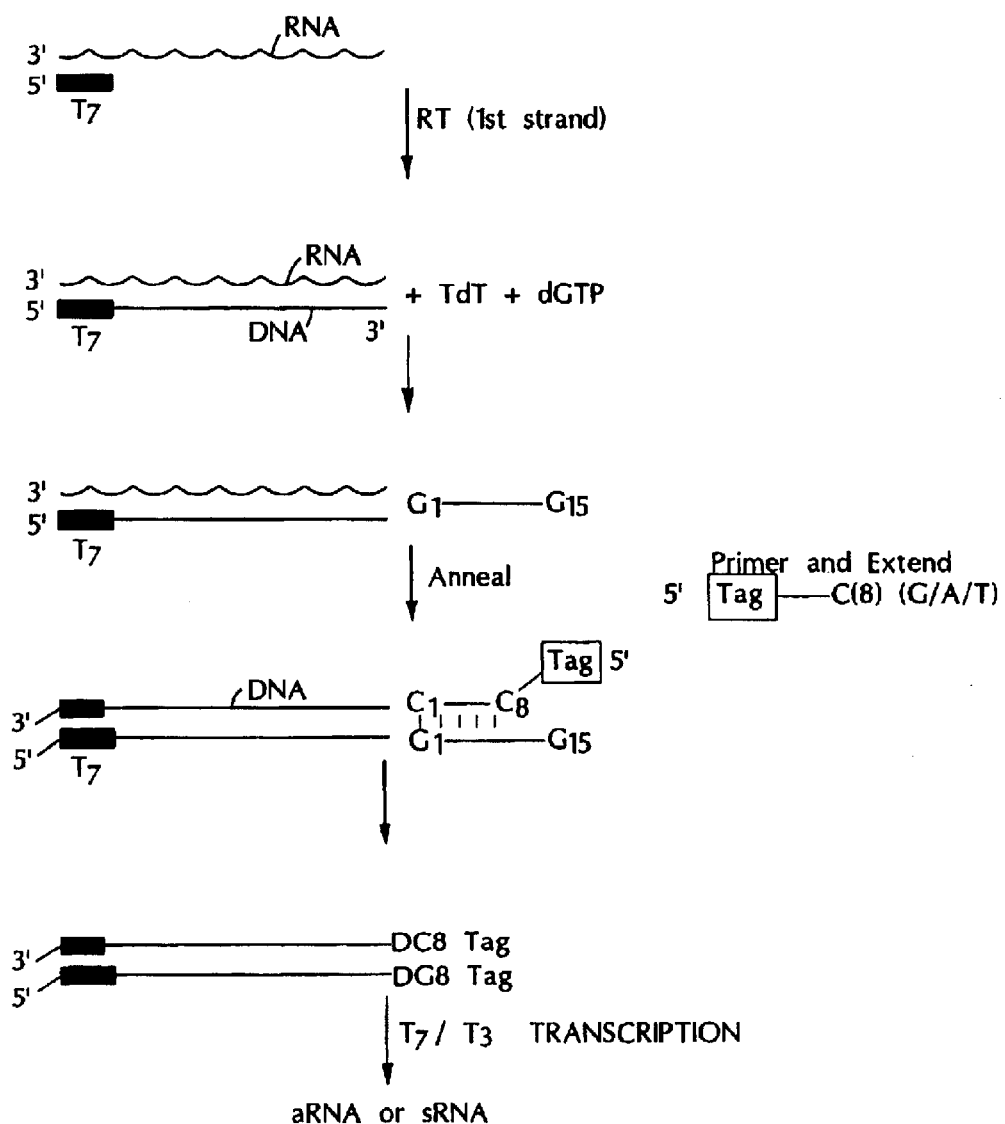
FIG. 11 is an exemplary transcription method for producing aRNA and/or sRNA.

Joining of the adaptor can be implemented in a variety of ways. For example, DNA and RNA ligases can be used (e.g., to ligate a preformed duplex that includes the tag sequence). In one embodiment, shown in FIG. 11, terminal transferase and dGTP are used to add a homopolymeric G tail to the DNA strand. An oligonucleotide that includes the tag sequence and a 3' polymeric C tail is annealed and used to prime synthesis of the second DNA strand.

In some implementations, it is also possible to detect a nucleic acid replicate made from a template by hybridization of a probe that is complementary to an adaptor sequence.

Insoluble Supports

As described herein, many embodiments include producing templates for RNA transcription that are attached to support. The insoluble support can be composed of any insoluble material. In one example, the insoluble support is a rigid planar device such as a chip (e.g., a microscope slide). In another example, the insoluble support is a reaction vessel such as a multi-container sample carrier (e.g., a microtitre plate), tube, column, spin-cup, disposable pipet tip, ring, disc (e.g., paper disc), lantern, pestle, membrane, or portions thereof. For example, the templates can be attached to a surface within one or more microtitre wells (e.g., in a variety of formats, including single, strips, 96-well, 384-well, robotically manipulated single or multiple plates). The microtitre plates can conveniently be placed into thermocontroller units, e.g., thermocyclers in order to finely control reaction temperatures.

In one embodiment, a spin cup is used. The cup has a porous membrane, e.g., a 0.45 μm membrane or any size membrane that facilitates passage of macromolecules such as the reaction enzymes. To conduct a set of multiple reactions, the reaction components are passed through the membrane (e.g., by low-speed centrifugation). To switch reaction components, buffer or a subsequent reaction mixture is washed through the membrane. The SSP oligonucleotide is first physically attached to the membrane (e.g., by a non-covalent or covalent linkage). Thus, throughout the reactions the SSP oligonucleotides and templates that incorporate them remain within the membrane of the spin cup. After templates are generated, the membranes can also be archived, e.g., for subsequent RNA transcription. Transcription products can also be collected by low speed centrifugation of the spin cup.

In another embodiment, a pin or set of pins is used. The SSP oligonucleotides are physically attached to the pins. For example, the SSP oligonucleotides are biotinylated and the pin surface is coated with a streptavidin. To process multiple reactions, multiple pins can be rigidly fixed to a holding unit. The holding unit is used to transfer to pins to different reaction mixtures. For example, the holding unit can be a lid of a microtitre plate. The lid is placed on different plates, each plate including appropriate reaction mixtures (e.g., for sample hybridization, reverse transcription, second strand synthesis, and transcription). For cyclic TCR, alternating pins, each pin for capturing T7 and T3 templates.

Figure 13:
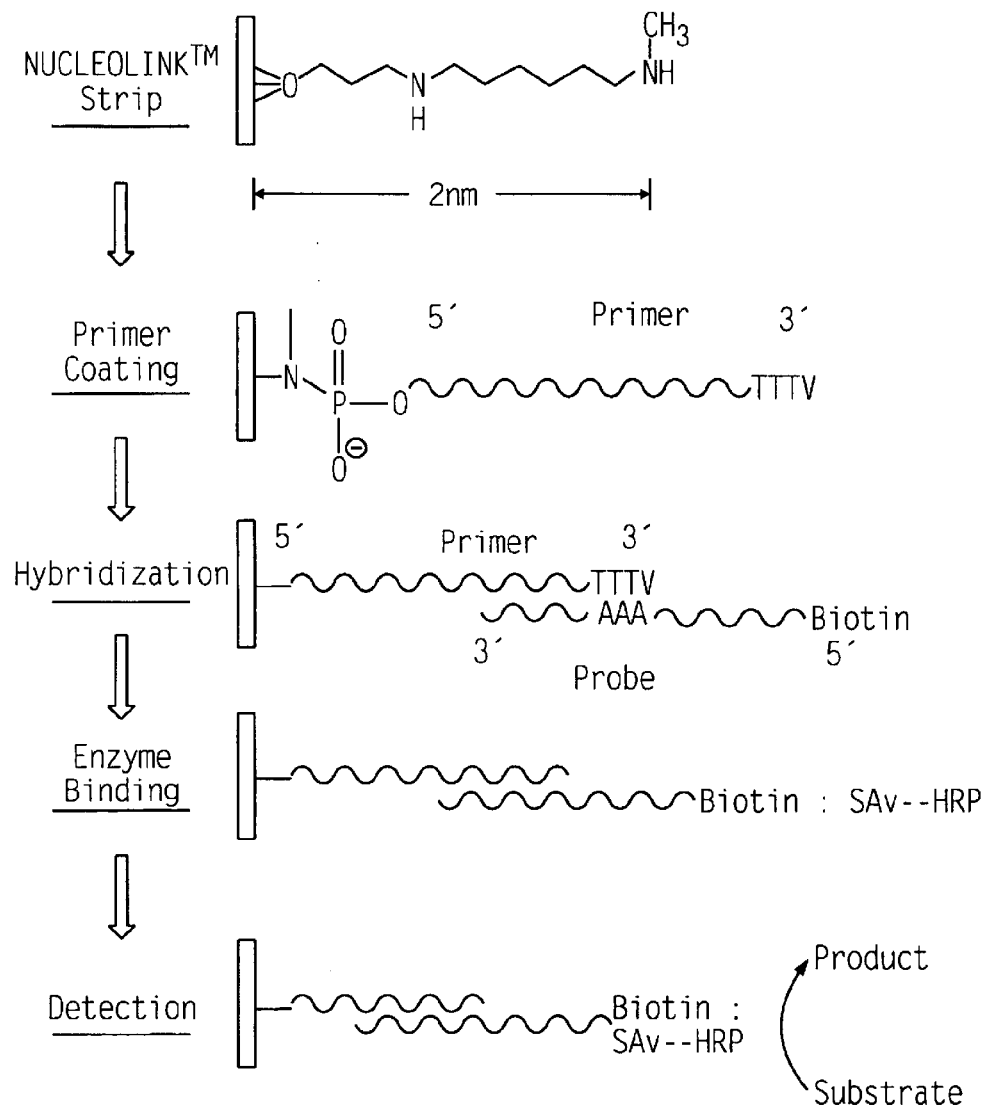
FIG. 13 is an exemplary method for evaluating the coupling of an oligonucleotide to an insoluble support.

Insoluble supports can be evaluated by hybridizing a probe that contains a sequence complementary to the primers on the support. See, for example, FIG. 13. For example, to detect the target binding activity of an immobilized primer, a probe oligonucleotide of 5'-biotin GCGCCAAT-TATCGAAAAAAAAAAAAAAAAAAAAA (SEQ ID NO:27) is allowed to hybridize with the primer on the insoluble support. The hybridized complex is washed with buffer, and then treated with a streptavidin-horse radish peroxidase conjugate. After the reaction between streptavidin and biotin molecules are completed on the insoluble support, the unbound enzyme conjugates are washed away. A solution containing o-phenylenediaminc and hydrogen peroxide is then added to the insoluble support. Color development of the solution is measured to indicate the quantity of streptavidin enzyme conjugate bound to the insoluble support. This in turn indicates the amount of biotin bound to the insoluble support which indicates the binding activity of the TCR primer on the insoluble support.

Detection Methods

A variety of detection methods can be used to analyze the RNA products of the amplification, or the reverse-transcribed DNA copies of the RNA products. Exemplary methods include single base extension (U.S. Pat. No. 6,013,431), mismatch detection (e.g., using MutS protein or other mismatch binding protein), sequencing by hybridization (U.S. Pat. No. 5,202,231 and PCT 89/10977) and RNA sequencing. Pastinen et al., supra describes an allele specific detection method in which two primers are annealed to the target. The primers differ only at the 3' most end which is complementary to the query site if the primer is directed to the allele that is present. Labeled nucleotides are only added to the primer in an extension reaction, e.g., using reverse transcriptase, if the primer is complementary at the query site.

To analyze a profile of sample nucleic acids, labeled RNA products can be generated from a template array to replicate the sample nucleic acids. The replicates are hybridized to a detection array that includes a plurality of capture probes. The detection array can be scanned to determine whether and to what extent the labeled RNA products hybridize to the probes. Because each probe is at a unique address, the amount of each species can be inferred. Methods for hybridization to detection arrays are well known. The information obtained by analyzing the detection array can be stored in a machine-accessible medium, e.g., with a pointer to information about the location or identify of an archival template array that can be used to make RNA replicates of the sample nucleic acid.

Paired-Probe Arrays

One implementation of the invention includes preparing sense and anti-sense nucleic acid from a nucleic acid sample, e.g., from a sample of mRNA. The mRNA is amplified using an array of immobilized SSP oligonucleotides. A T7 promoter-poly d(T) SSP oligonucleotide hybridizes to the polyadenylated 3' region of mRNA, dsDNA is synthesized and a TCR adaptor is ligated to the free end. The dsDNA is then transcribed to produce labeled anti-sense RNA. The anti-sense RNA can also be hybridized to an array that includes a TCR-adaptor complementary region arid a RNA polymerase promoter. Labeled sense RNA is produced from this hybridization as described.

For example, the labeled anti-sense RNA is hybridized to an array of sense probes(e.g., an "soligo Microarray") and the labeled sense RNA is hybridized to an array of anti-sensc probes (e.g., an "aOligo Microarray"). Data is collected from the two hybridizations and compared. For example, a transcript ratio is determined for a given gene in two different tissue samples using the labeled anti-sense RNA; and another transcript ratio is determined for the given gene in two tissue samples using the labeled sense RNA. The two ratios are then compared, e.g., to determine a reliability coefficient ($R_c$). $R_c$ values between 0.8 and 1.0 can be indicative of a reliable observation.

Other types of ratios can also be determined. For example, for a single sample, the ratio of levels of hybridization of the labeled sense RNA to probe A and probe B can be compared to the ratio of level of hybridization of the labeled anti-sense RNA to probe A' and B', where probe A and A' are complementary and B and B' are complementary. The probes can be partially or non-overlapping probes to the same gene (e.g., transcript), or can be probes to different genes. In one embodiment, one of the genes is a housekeeping gene or other gene whose expression level provides a useful reference.

dsRNA

In one embodiment, double-stranded RNA is produced for one or a plurality of target sequences. The dsRNA can be delivered to cells or to an organism. Endogenous components of the cell or organism can trigger RNA interference (RNAi) which silences expression of genes that include the target sequence. It is well established that many cells and organisms have an RNAi response (e.g., nematodes, plant cells, and mammalian cells). Individual target sequences can be annealed to SSP oligonucleotides on different insoluble supports (e.g., different microtitre wells or different pins) in order to generate templates for aRNA and sRNA. These templates can be made separately or on the same support. Transcription of these templates produces aRNA and sRNA that hybridize to each other to produce dsRNA. If the aRNA and sRNA are produced separately, it may be useful to denature the RNAs and annealed them to form the dsRNA duplex. In some cases, the templates are produced in pools thereby producing a mixed population of dsRNA. In other cases, individual species of dsRNA are produced so that each target sequence can be separately attacked. The individual species can be correspond to different transcripts of an organism or cell, or may correspond to different regions within the different transcripts. Some species can be splice variant specific.

In one embodiment, the templates are immobilized in a regular array such that each address of the array includes a substantially homogenous population of templates. Cells (e.g., mammalian culture cells) can be grown on the array so that dsRNA made by each address of the array can enter the cell. After incubation, the cells can be evaluated to determine the effect of the dsRNA on the cells. The regular array format can be, e.g., a microtitre plate.

In one embodiment, dsRNA is made for a substantial portion of a transcriptome. In this case, the plurality of targets is the corresponding portion of the transcriptome. These dsRNAs can be used, for example, to characterize the biological function of different members of the transcriptome.

Again, the templates used to produce the dsRNA can be archived and also produced as master and slave sets. The slave sets can be distributed to different users who can produce dsRNA on demand. Because the template are immobilized, the dsRNAs can be washed from the insoluble supports and used directly, e.g., contacted to cultured cells or cell in an organism.

In one embodiment, a multi-well plate is used. Each well of the plate includes an immobilized SSP oligonucleotide. Different nucleic acids are deposited in each well of the plate and annealed to the SSP oligonucleotide (e.g., by hybridization to a target region of the SSP oligonucleotide) to form an annealed complex. A template is generated from the annealed complex, e.g., using a DNA polymerase (and if the added nucleic acid is RNA by reverse transcription). A second promoter is joined to the annealed complex or template so that ultimately a template is formed with a promoter at both termini. The second promoter can be the same or different from the promoter of the SSP oligonucleotide. RNA polymerase is then added so that transcripts are made from both strands of the template. The transcripts are annealed to each to form dsRNAs.

Exemplary applications for dsRNAs include target validation and therapeutic use.

Fragment Preparation

Referring to FIG. 1, another exemplary implementation of the invention is set forth. This implementation is directed to the analysis of genomic DNA, e.g., for polymorphisms. The implementation includes: fragment preparation 10, rendering the sample single-stranded 12, SSP oligonucleotide annealing 14, attachment 16, transcription 18, and detection or analysis 20.

Genomic DNA is isolated from cells, e.g., from a subject such as a human patient. The DNA is digested using restriction enzymes to generate target fragments. To amplify multiple fragments from the genomic DNA, restriction enzymes are selected based on one or more of the following criteria. The target fragments are less than about 2000, 1000, 500, 700, 500, 300, 200 or 100 nucleotides in length. The target fragment includes at least about 15, 18, 20, or 22 nucleotides of non-polymorphic nucleotide sequence in proximity to the restriction site. Such non-polymorphic regions can function as annealing sites for the SSP oligonucleotide. The polymorphism of interest is located within the central two-thirds of the target fragment. If multiple restriction enzymes are required, the restriction enzymes can be chosen that are compatible, e.g. functional at the same reaction conditions.

Figure 2:
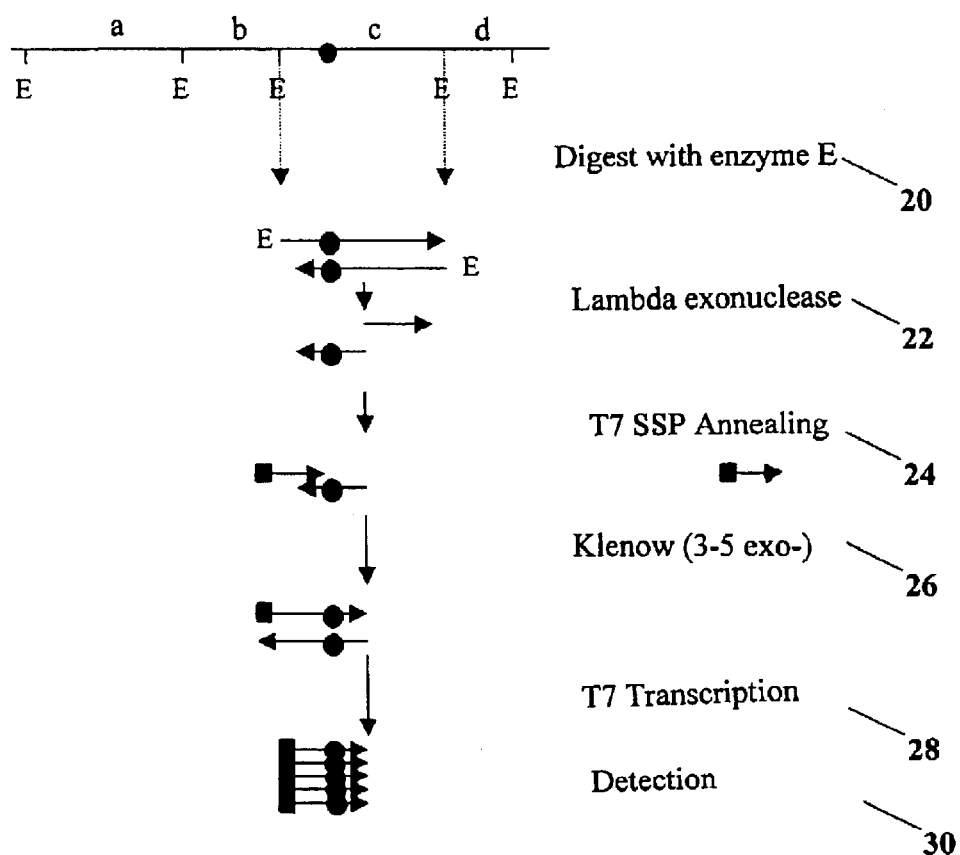
FIG. 2 is a schematic of the steps in an exemplary SSAT method.

Referring to the example depicted in FIG. 2, enzyme E cuts the DNA into fragments, labeled "a", "b", "c", and "d". Fragment "d" contains a sequence of interest that, for example, includes a polymorphism represented by a closed circle.

In one embodiment, prior to annealing of the SSP oligonucleotide to the sample nucleic acids, the cleaved sample nucleic acids are rendered as single stranded. The production of single-stranded DNA can be achieved by heat or chemical denaturation. However, enzymatic means for producing single-stranded DNA were found to be particularly effective for the SSAT method.

The double-stranded DNA fragments are treated with an exonuclease, such as T7 exonuclease or lambda exonuclease. For example, the cleaved sample nucleic acids can be treated with lambda exonuclease for about 1 hour at 37° C. These exonucleases catalyze digestion of DNA in the 5' to 3' direction, thereby sequentially removing 5' mononucleotides from duplex DNA (Little, JW (1981) *Gene Amplification and Analysis* 2:135–145; Shimozaki and Okazaki. (1978) *Nucl. Acids. Res.* 5:4245–4261). The reaction can be inactivated by heating at 75° C. for 30 minutes.

Lambda exonuclease is a highly processive enzyme. As such, it has a strong predilection to remain attached to a substrate DNA strand and digest it to completion before dissociating and attacking another substrate DNA. This feature results in longer single stranded DNA products rather than multiple fragments that are a fraction of the size of the input DNA. The processivity of various exonucleases is described, e.g., in Thomas and Olivera (1978) *J Biol Chem* 253:424–9.

The processed single stranded DNA products are used as samples for amplification, e.g., as described above.

Software

Also provided is a system and software which can assist, control, and manage one or more steps of the method described herein.

Figure 4:
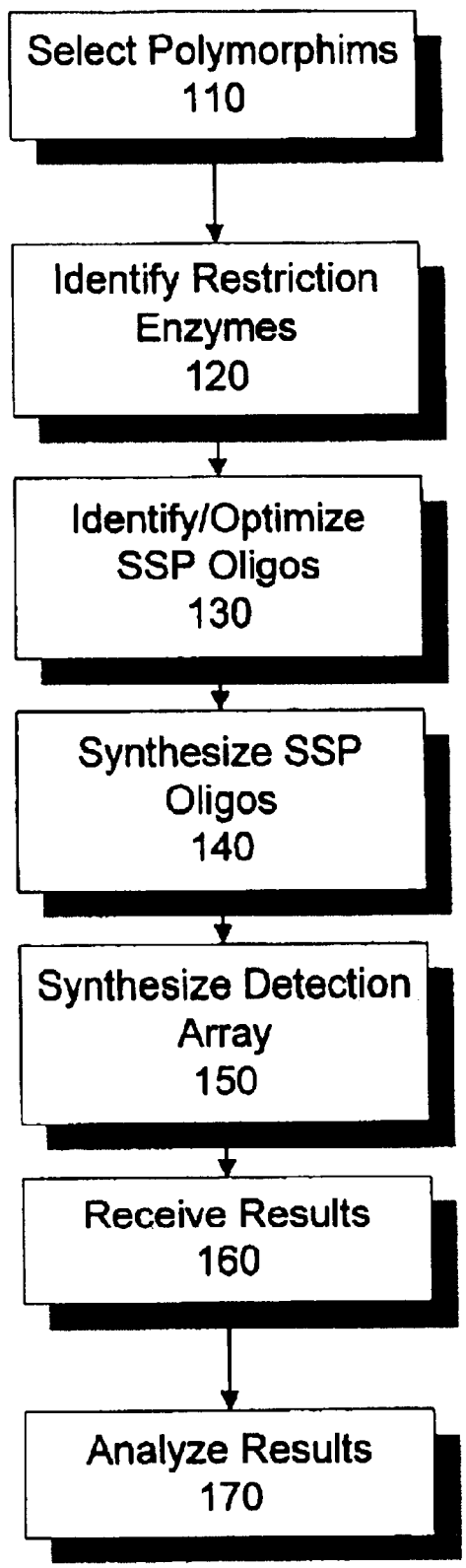
FIG. 4 is a flow chart of modules that are implemented by an exemplary system.
Figure 5:
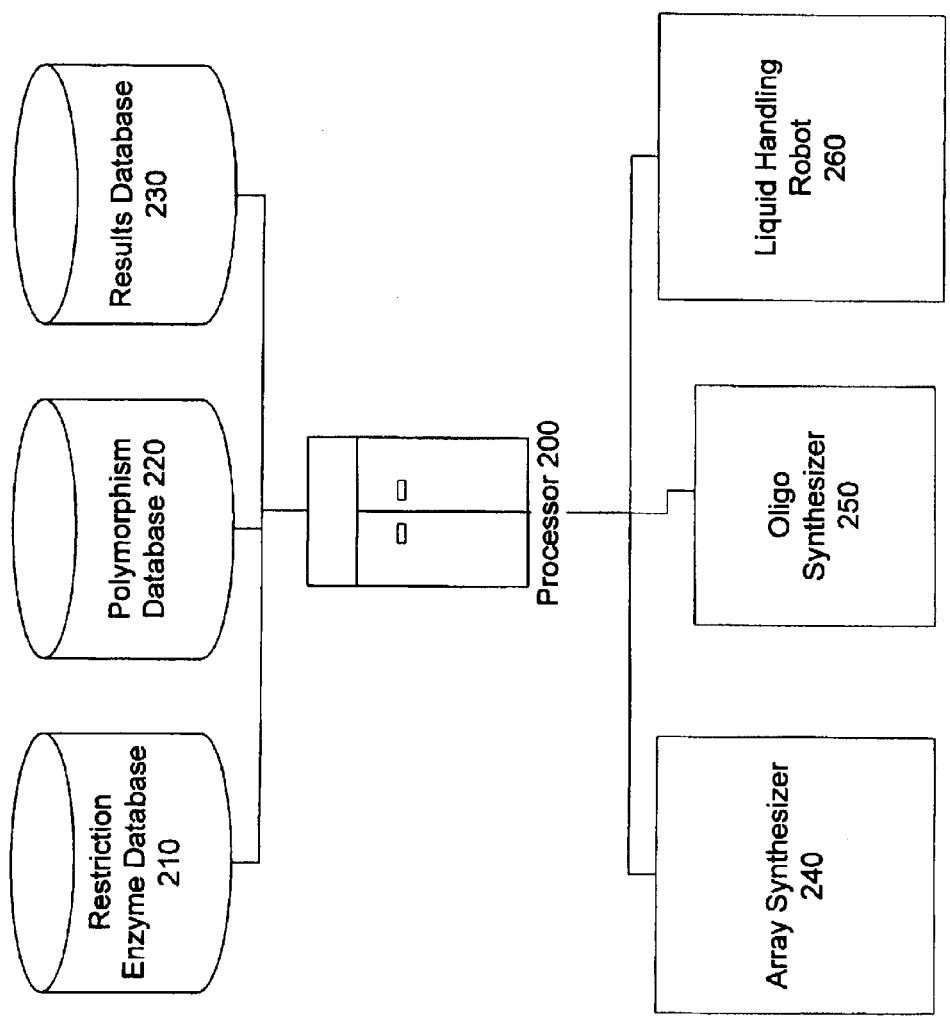
FIG. 5 is a schematic of an exemplary system.

Referring to FIGS. 4 and 5, software can include modules for one or more of the following: (1) selecting polymorphisms for analysis 110; (2) identifying restriction enzymes for fragment preparation 120; (3) identifying and, optionally, optimizing SSP oligonucleotide design 130; (4) interfacing with an oligonucleotide synthesizer or oligonucleotide array synthesizer to produce SSP oligonucleotides 140; (5) synthesizing a detection array 150; and (6) receiving 160 and analyzing 170 results from the detection array.

The software can be implemented by a processor 200 running on a networked server or locally on a desktop computer. The processor is interfaced with databases 210, 220, and 230. These databases can be stored in local memory, on machine-readable media, or on remote servers. The processor is also, directly or indirectly, interfaced with external apparati, for example, an array synthesizer 240, an oligonucleotide synthesizer 250, or a liquid handling robot 260.

The software can include a graphical user interface (GUI) that displays known polymnorphisms, e.g., SNPs for user selection. The polymorphisms can be pre-grouped based on relevance for various diagnostic, disease, or gene-mapping projects. The user can select one or more of the groupings as desired.

Polymorphism information can be stored in a database 220 of polymorphisms. For each polymorphism, the database 220 can also indicate one or more precalculated items of information. Such information can include the availability one or more restriction enzymes which can be used to fragment genomic nucleic acid in order to produce a fragment of desired size. Multiple local restriction enzyme sites can be stored in order to allow optimization of overall restriction enzyme selection such that enzymes that function in compatible buffers can be pooled. The database 220 can also store information about optimal SSP oligonucleotide target sites for each available restriction site. Alternatively, this information can be determined after polymorphism selection.

For example, the process 120 for identifying appropriate restriction enzymes can include searching a database 210 of restriction enzyme information to identify restriction enzymes that digest near a polymorphism site in order to produce a fragment of appropriate size. The restriction enzyme database 210 includes information about the specific recognition sites of each enzyme, and its compatibility with various buffer conditions. The database can include, for example, information from the database that was established by Roberts et al. (Nucl. Acids. Res. 2001, 29:268–269) and includes information for over 3000 enzymes.

After polymorphisms are selected, the system can output an optimized combination of restriction enzymes to be used to fragment the sample nucleic acid. The software can, in some embodiments, also control a robotic system to prepare the determined restriction enzyme pool.

The system also designs one or more SSP oligonucleotides for each polymorphism. The system can optimize primer design for $T_m$, e.g., so all target binding regions of a group of SSP oligonucleotides have a similar $T_m$, primer dimer formation, absence of palindromes, and so forth. The system can be interfaced with an oligonucleotide synthesizer to produce the SSP oligonucleotides or oligonucleotide array synthesizer to produce an array of immobilized SSP oligonucleotides.

Similarly, a related, or even the same system can be used to process information for nucleic acids detected on paired complementary arrays. The system can be used to maintain a database that includes data representing hybridization to a sense probe, and hybridization to an antisense probe, and relationships between the sense and anti-sense probe. The database can also include a ratio between hybridization levels for a first and second target material to their corresponding sense probes and a ratio between hybridization levels for the first and second target material to their corresponding anti-sense probes. As described above, the hybridization material is appropriately generated for each probe set.

In another aspect, the invention features a system that provides access to a database that includes information about transcript levels for a plurality of genes. The database can include records that include a reference describing a sample (e.g., tissue source, tissue type and so forth), a reference to a profile (the profile being a table describing transcript levels for the plurality of genes), and a locator indicating the identity or location of the support that includes archived templates that can be transcribed to produce aRNA or sRNA corresponding to the sample. The database can include at least ten records, e.g., each referring to a different mammalian tissue. In some embodiment, each sample is microdissected. In some implementations, the insoluble support can be provided to a user (e.g., a customer) in combination with access to the database, particularly to the record referring to that particular insoluble support. Database access can be provided in a variety of ways, e.g., by distribution of an access code (e.g., for Internet access) or by distribution of a machine readable medium that includes the records themselves.

Array Synthesis

Some embodiments use one or more arrays, for example: (1) an array of SSP oligonucleotides; and (2) a detection array (e.g., a polymorphism or transcript detection array). An array can be an insoluble support that includes a plurality of addresses. Each address can include a homogenous population of immobilized nucleic acids, e.g., nucleic acids of predetermined sequence. The density of addresses can be at least 10, 50, 200, 500, $10^3$, $10^4$, $10^5$, or $10^6$ addresses per $cm^2$, and/or no more than 10, 50, 100, 200, 500, $10^3$, $10^4$, $10^5$, or $10^6$ addresses/$cm^2$. Addresses in addition to addresses of the plurality can be deposited on the array. The addresses can be distributed, on the substrate in one dimension, e.g., a linear array; in two dimensions, e.g., a planar array; or in three dimensions, e.g., a three dimensional array. (e.g., layers of a gel matrix).

In one embodiment, the substrate is an insoluble or solid substrate. Potentially useful insoluble substrates include: mass spectroscopy plates (e.g., for MALDI), glass (e.g., functionalized glass, a glass slide, porous silicate glass, a single crystal silicon, quartz, UV-transparent quartz glass), plastics and polymers (e.g., polystyrene, polypropylene, polyvinylidene difluoride, poly-tetrafluoroethylene, polycarbonate, PDMS, acrylic), metal coated substrates (e.g., gold), silicon substrates, latex, membranes (e.g., nitrocellulose, nylon). The insoluble substrate can also be pliable. The substrate can beopaque, translucent, or transparent. In some embodiments, the array is merely fashioned from a multiwell plate, e.g., a 96 or 384 well microtitre plate.

The array of SSP oligonucleotides has an SSP oligonucleotide at each address such that the promoter is accessible and functional and the target binding region is able to specifically recognize the target site. In some embodiments, the 3' terminus of the SSP oligonucleotide is extendable, e.g., by a DNA polymerase when hybridized to a template. The SSP oligonucleotide can be anchored to the array substrate at the 5' terminus. Alternatively, the SSP oligonucleotide can be anchored to the array substrate at a non-terminal nucleotide, so long as the above preconditions are satisfied. In other embodiments, the 3' terminus is non-extendable.

One method of anchoring SSP oligonucleotides requires synthesizing an amino-modified nucleotide. During the phosphoramidite synthesis, at the desired position, an amino-modified nucleotide is included. The resulting amino-modified SSP oligonucleotide is then deposited on a surface activated to covalent couple to amino groups. Such a surface and method are described in provisional patent application, U.S. Ser. No. 60/293,888, filed May 24, 2001. The surface is characterized by a covalently bonded activated group that includes an electron-withdrawing group on an N-substituted sulfonamide.

A second method of anchoring SSP oligonucleotides requires synthesizing the SSP oligonucleotides directly on an insoluble support using a 5'→3' synthetic method, such as the method described in PCT US 01/02689. This method provides nucleotide arrays having C-5' bound to the surface and C-3' at the terminus. The arrays can be produced by reacting C-5' activated, C-3' photolabile group protected nucleotides, with a terminal hydroxyl group bound to the surface. After coupling a modified nucleotide to the surface, the C-3' photolabile protecting group can be deprotected via a photochemical reaction to form a free hydroxyl group at the C-3' terminus. The hydroxyl group, in turn, can react with a modified nucleotide including a C-5' phosphorous activating group to tether the modified nucleotide to the surface. Repeated selective coupling of modified nucleotides carrying a C-5' phosphorous activating group, such as phosphoramidite, and selective photodeprotection of the C-3' photolabile protecting groups forms immobilized oligonucleotides arrays having C-5' attached to the solid surface and the C-3' at the terminal position. Selective photodeprotection can be accomplished by several known methods, e.g. photolithography methods (as disclosed in Science (1991) 251:767–773; Proc. Natl. Acad. Sci. USA 93:13555–13560, (1996); U.S. Pat. Nos. 5,424,186; 5,510,270; and 5,744,305, and 5,744,101) or a digital micromirror technique (e.g., as described in Sussman et. al. (1999) Nature Biotechnology 17:974–97).

A third method of forming an SSP array includes the deposition of an unmodified oligonucleotide on a substrate. Numerous methods are available for dispensing small volumes of liquid onto substrates. For example, U.S. Pat. No. 6,112,605 describes a device for dispensing small volumes of liquid. U.S. Pat. No. 6,110,426 describes a capillary action-based method of dispensing known volumes of a sample onto an array.

In addition to these exemplary methods, any of the applicable array synthetic method can be used so long as the oligonucleotide is functional as a promoter and the target binding region is specific for the target site.

The second type of array includes a plurality of detection probes. The probes can be designed in any of a number of formats to detect SNPs or mRNA. For example, a pair of probes can be used for each biallelic SNP. Each pair has the appropriate nucleotide at the query position to detect one of the two alleles. The query position can be at the terminus of the detection probe. In another embodiment, the detection probe is a primer, and base extension protocols, e.g., as described in (Law and Brewer (1984) Proc. Natl. Acad. Sci. USA 81:66–70; Pastinen el al. (2000) Genome Res. 10:1031–1042) are used to assess which allele is present. In still another embodiment, the query position is more centrally located, and the detection probe can be used, for example, as.described in U.S. Pat. No. 5,968,740.

Uses

The methods and arrays described here can be used for transcription amplification. One exemplary application is genotyping to investigate the presence of single nucleotide polymorphism (SNP) within a gene. The significance of SNPs is described in Weaver, *"High-throughput SNP Discovery and Typing for Genome-wide Genetic Analysis"*, Trends in Genetics, December 2000). The detection of polymorphisms has a variety of applications. Non-limiting examples include medical diagnostics, forensics, disease gene mapping, environmental management, agriculture, and protein evolution. Another exemplary application is evaluating transcripts in a sample, e.g., a sample that includes cells, e.g., fewer than 10 000 or 1 000 cells.

mRNA Libraries

One exemplary application of the invention is the amplification, analysis and archiving of mRNA populations. This process enables the high throughput amplification and detection of mRNA from small amounts of starting material, e.g., less than 1 pg, 100 ng, 10 ng, or 1 ng. For example, the process can be used to profile the expression of genes in a single cell. Further, the process results in an archive of the input nucleic acid sample. The archive can be repeatedly transcribed, to permit analysis of the sample. The mRNA population can be amplified using an immobilized oligonucleotide primer as a reverse transcription primer, e.g., as described above.

The benefits of the application are numerous. For example, the method does not require a number of manipulations such as precipitations and spin column separations. The washing and exchange of solutions is simplified as the cDNA archive is immobilized on the insoluble support. Washing also removes unbound targets, such as ribosomal RNA, which can interfere in reverse transcription by providing sites for non-specific priming.

The insoluble support serves as a DNA archive of the original mRNA sample. The archive can be returned to, time and again. Moreover, the archive is amplified by transcription, which restores the original sample in its RNA state. Such amplification is also linear and may be less susceptible to biasing events than, e.g., exponential amplification. In some embodiments, the method is supported by a single primer for reverse transcription. The primer is universal for all polyadenylated mRNAs.

In one embodiment, the method is used to archive an mRNA sample from a limited number of cells, e.g., fewer than 100 cells, e.g., a single cell. The DNA archive of the mRNA sample (or a sample of any nucleic acid) can be constructed for, e.g., normalized libraries, subtracted libraries and reduced complexity libraries.

RNA replicates generated from the insoluble support can be used, e.g., for profiling transcripts in the original mRNA sample, in vitro translating transcripts representative of transcripts in the original mRNA sample, and generating dsRNA.

In one embodiment, RNA replicates (aRNA or sRNA replicates, as appropriate) are used in a subtractive hybridization reaction. For example, aRNA replicates from a first sample can be subtracted from sRNA replicates produced from a second sample or from DNA produced from a second sample. Methods for subtractive hybridization are well known (e.g., one set of replicates can be attached to an insoluble support). In one embodiment, the method includes two subtraction hybridizations, one forward (e.g., aRNA vs. sRNA), the other backward (e.g., sRNA vs. aRNA). The net result is a highly differential comparison.

All cited references, patents, and patent applications are incorporated by reference in their entirety. Accordingly, U.S. application Ser. No. 60/312,443, filed Aug. 15, 2001; 60/338,523, filed Nov. 5, 2001; 60/373,364, filed Apr. 16, 2002; and Ser. No. 10/219,616 filed Aug. 15, 2002, are incorporated by reference in their entirety. The following examples illustrate the specific embodiments of the invention described herein. As would be apparent to persons skilled in the arts, various changes and modifications are possible and are contemplated within the scope of the invention described.

EXAMPLE 1

Preparation of Aminopropylsilylated CPG Beads 10 g CPG beads (906 A, 80–128 mesh) were heated at 80° C. for 3 hr, cooled under nitrogen to the ambient temperature, and packed in a 25 mm×120 mm glass wool insulated HPLC column. 80 mL of 1:7 3-aminopropyltriethoxysilane and dry toluene were heated to around from 54° C. to 98° C. in a heated flask and then continuously pumped through the CPG beads packed column. The temperature of the column was monitored at around 37° C. to 45° C. during the course of reaction of about 38 hr. After the reaction was completed, the packed CPG beads were washed in the column twice with 125 mL methanol and twice with 125 mL acetone, and poured into a glass container. After drying under high vacuum in the glass container, the beads were stored under nitrogen ready for next synthesis.

Preparation of 3-(3(N-cyanoethyl-toluenesulfonamido-carbonyl) propyl-carboxamido-propylsllated CPG Beads 0.5 g of the above aminopropylsilylated CPG beads, 200 mg of 3-(toluenesulfonamido-carbonyl) propionic acid, 400 mg of Bop, and 4 mL dry NMP, and 0.25 mL diethylpropylamine were charged to a 6 mL reaction vial in a glove box. After shaking gently for about 3.5 hr, the CPG beads were transferred to a filtering cartridge, drained, and washed twice with 6 mL acetone, twice with 6 mL NMP, three times with 6 mL acetone. After drying under high vacuum, the beads were transferred to a 6 mL reaction vial. The beads were then treated with 4 mL dry NMP and 0.25 mL chloroacetonitrile and 0.25 mL diethylpropylamine, and shaken gently at the ambient temperature for about 21 hr. The CPG beads were transferred to a filtering cartridge, drained, and washed twice with 6 mL NMP, four times with 6 mL methanol, and twice with 6 mL acetone. After drying under high vacuum for 2 hr, the CPG beads were ready for solid phase covalent bonding reactions.

Experimental: CPG beads were activated. 100 pmols of AmC6N12T7dT20V oligo primers were coupled onto 4 mg of GPG beads in 400 mM sodium carbonate buffer at pH 9.5 for 1 hour at room temperature, followed by incubation overnight at 4° C. The beads were then blocked for two hours in blocking buffer, which contain 50 mM ethanolamine, 0.1 M Tris, and 0.1% SDS pH 9.0. After blocking, the beads were washed several times in Tris-buffered saline and either use immediately, or store in 70% ethanol. cDNA synthesis and transcription were carried out as described.

The sequence of [AmC6]N12T7dT20V: is as follows:

5'-[AmC6]ATAGGCGCGCCAATTAATACGACTCAC
TATAGGGAGATTTTTTTTTTTTTTTTTTV-3'
(SEQ ID NO:28)

Results: Covalently coupled promoter primers, which contain a PEG linker and a 12 base spacer, were used successfully for template preparation and transcription from the CPG beads.

EXAMPLE 2

Covalent Coupling of TCR Primer to Microtitre Strips

TCR primer oligonucleotides with the following sequences were synthesized.

N12 Primer

5'-ATAGGCGCGCCAATTAATACGACTCACTATAG
GGAGATTTTTTTTTTTTTTTT TTTV-3' (SEQ ID NO:29)

N25 Primer

5'-ACGTACGTACGTCATAGGCGCGCCAATTAATA
CGACTCACTATAGGGAGATTTTTTTTTTT
TTTTTTTV-3' (SEQ ID NO:30)

N50 Primer:

5'-ACGTACGTACGTACGTACGTACGTCACGTACG
TACGTCATAGGCGCGCCAATTAATACGACTCA
CTATAGGGAGATTTTTTTTTTTTTTTTTTTV-3'
(SEQ ID NO:31)

Each oligonucleotide was phosphorylated at the 5'-end and purified by HPLC method individually. Each 5'-phosphorylated primer was then diluted to 100 nM in 10 mM 1-methylimidazole (pH 7.0) and the solution was added with 20 mM EDC. Each coating mixture was then pipetted to NUCLEOLINK™ aminated strips (from Nalge Nunc International, Rochester, N.Y.): 100 μL per well. All the primer coupling reactions were continued at 42° C. for 4 hours. Each empty well was washed once at room temperature, soaked for 5 minutes at 42° C., and washed three more times at room temperature, all with 20 mM PBS (pH 7.4)/0.1% Tween 20/0.5% bovine γ globulin (BgG.) To remove salt residues, the empty wells were washed three times with MILLIO™ (Millipore Corp., Billerica, Mass.) water. The dry primer coated strips were stored at 4° C. until use.

To investigate the binding activity of TCR primer coated on the microtitre wells, samples of probe oligonucleotide of 5-Bt-GCGCCAATTATCGAAAAAAAAAA AAAAAAAA (SEQ ID NO:32) were prepared in PBS/O. 1% Tween 20/0.5% BgG, at the following concentrations: 0, 0.28, 0.56, 1.4, 2.8, 5.6, and 50 nM. The hybridization and detection assays were carried out in triplicates according to the following procedure.

1. Pipet 20 μL of biotinylated probe sample into each well.
2. Incubate at 42° C. for 30 minutes.
3. Wash 3 times with 100 μL of 2×SSC/0.1% Tween 20 buffer.
4. Pipet 20 μL of Streptavidin-horse radish peroxidase conjugate solution (Pierce Chemical), 0.2 μg/mL in PBS/0.05% Tween 20, into each well.
5. Incubate at room temperature for 30 minutes.
6. Wash once at room temperature, soak at 42° C. for 20 minutes, and then wash 3 more times, all with 100 μL of PBS/0.1% Tween 20/0.5% BgG.
7. Pipet 50 μL of 1.5 mM o-phenylenediame in 1×stable substrate (Pierce Chemical), into each well.
8. Incubate at room temperature for 15 minutes.
9. Add 150 μL of 0.5M Sulfuric acid to each well.
10. Measure absorbance at 492 nm on a microplate reader.

Results: The averaged absorbance from the triplicates of each sample is shown in the Table 2 below.

TABLE 2

Detection of Immobilized Oligonucleotides

| Probe Conc. (nM) | Absorbance |
| --- | --- |
| 0 | 0.015 |
| 0.28 | 0.835 |
| 0.56 | 1.303 |
| 1.4 | 1.708 |
| 2.8 | 2.094 |
| 5.6 | 2.224 |

This dose dependency of biotin probe concentration demonstrated a robust assay with 3 log-orders of dynamic range and also specific target binding activity for the primer immobilized on the insoluble support.

The microtitre strips coated with three different TCR primer oligonucleotides were used to amplify human liver RNA according to the following procedure.

1. 500 ng human liver RNA (Ambion, Inc. Austin, Tex.) was annealed to insoluble support anchored oligos in the presence of first strand synthesis buffer and DNase inhibitor was used in each of the two positive controls (1 μg per reaction.) The negative control was a well to which no RNA was added. mRNAs were annealed at 42° C. for 5 minutes.
2. cDNA synthesis was initiated by adding sodium pyrophosphate, and AMV reverse transcriptase. (Promega Catalog No. C4360)
3. Reactions were incubated at 42° C. for 1 hour.
4. Second strand cDNA synthesis was initiated by the addition of 40 μL of 2.5× second strand synthesis buffer (1×=40 mM Tris-HCl, pH 7.2); 5μL of 1 mg/mL acetylated BSA; 23 units of DNA polymerase 1; 0.8 unit of RNase H, and nuclease free water to final volume of 100 μL. Incubated at 14–16° C. for 2 hours.
5. Wells were washed several times with 50 mM Tris-HCl, pH 8.0. The wells were then placed on ice, and 20 μL 1×T7 RNA polymerase transcription buffer was added.
6. Transcription reactions were performed in 20 μL volume, by following protocol provided by the manufacturer (AMPLISCRIBE™ T7 HIGH YIELD TRANSCRIPTION KIT, Cat No. AS2607, Epicentre, Madison, Wis.) Reactions were incubated at 37° C. for 1–2 hours.
7. 5μL of the reactions was analyzed on an agarose gel.

Results: Agarose gel analysis revealed that RNA with a medium distribution between 0.4–1.0 kb was amplified by the N25 and N50 primers coated wells. N12 primer coated wells gave some amplification of RNA, but less than the amount by the N25 and N50 primers. See Table 3 below. No RNA transcripts were amplified by the negative controls.

TABLE 3

|  | Purified RNA | Estimated Amplification |
| --- | --- | --- |
| N12 Primer Coated Wells | 0.35 μg | 35 fold |
| N25 Primer Coated Wells | 1.91 μg | 191 fold |
| N50 Primer Coated Wells | 1.51 μg | 151 fold |

It was determined that the N25 primer coated wells repeatedly gave better amplification of RNA than N50 and N12 primers. The optimal length of the spacer is 25 nucleotides or a linker of equivalent length formed by a chemical substitute.

EXAMPLE 3

Blotinylated Primer Length

In these experiments, 5' biotinylated oligonucleotide primers containing a 0, 6, or 12 nucleotides spacer sequence between the biotin and the promoter sequence, were tested for their effects on transcription. Reaction conditions for cDNA and for transcription were similar to previously described. Oligo-primer densities tested were 10 pmols per well and 1 pmol per well. The amount of RNA used was, variously, 1 microgram and 500 ng per reaction.

Enhanced amplification was observed with the primers that include 6 and 12 nucleotide spacers (Bt(6)T7dT20V and Bt(12)T7dT20V) relative to the amplification observed with the primer having a 0 nucleotide spacer (Bt(0)T7dT20V).
Primer Sequences:
Bt(0)T7dT20V:
   5'-Bt-ATTAATACGACTCACTATAGGGAGATTTTTTT TTTTTTTTTTTTV 3' (SEQ ID NO:33)
Bt(6)T7dT20V:
   5'-Bt-GCGCCAATTAATACGACTCACTATAGGGA GATTTTTTTTTTTTTTTTTTV 3' SEQ ID NO:34
Bt(12)T7dT20(V):
   5'-Bt-ATAGGCGCGCCAATTAATACGACTCACTATA GGGAGATTTTTTTTTTTTTTTTTT TTTTV-3' (SEQ ID NO:35)

EXAMPLE 4

The solution mode of sequence specific amplification by transcription was used to amplify the StuI fragment of the human apolipoprotein E gene. (This fragment codes for amino acid 72 to amino acid 209).

Human genomic DNA was purchased from Sigma Chemicals (St. Louis, Mo.). Samples of 20 µl containing 10 µg high molecular weight human DNA were digested for 3 hours at 37° C., using 10 units of StuI (New England Biolabs, Beverly, Mass.). The StuI digests were diluted to 50 µl in the presence of 1× lambda exonuclease buffer (67 mM Glycine-KOH(pH 9.4), 2.5 mM MgCl$_2$, and 50 µg/ml BSA), and 10 units of lambda exonuclease (New England Biolabs, Beverly, Mass.) and incubated at 37° C. for 30 minutes. This enzyme reaction was terminated by incubation at 75° C. for 30 minutes.

Subsequently, the reaction mixture was further diluted to 100 µl in the present of 1× Klenow fragment (3'->5' exo) buffer (10 mM Tris-HCl (pH 7.5), 5 mM MgCl$_2$, 7.5 mM dithiothreitol), and 10 pmols of SSP oligonucleotide (SEQ ID NO: 1; T7StuSE), and hybridization was carried out at 37° C. for 10 minutes. The SSP oligonucleotide anneals to one end of the StuI fragment of the human apolipoprotein E gene (amino acid 72 to amino acid 209). The following is the sequence of the T7StuSE:

5'-AATTAATACG ACTCACTATA GGGAAGGCCT ACAAATCGGA ACTGGAG-3' (SEQ ID NO:1)

The T7 polymerase promoter is underscored. The apoE annealing site is 3' to the promoter.

After SSP oligonucleotide annealing, the primer and apoE target are extended by the addition of 10 units of Klenow fragment DNA polymerase (New England Biolabs, Beverly, Mass.), 10 mM each of dATP, dGTP, dTTP, and dCTP during incubation at 37° C. for 1 hour. After heat inactivation of the enzyme at 75° C. for 30 minutes, the mixture was adjusted to 2.5 M ammonium acetate, and two volumes of 100% ethanol were added to precipitate the DNA. DNA was then recovered by centrifugation and dissolved in 20 µl of 10 mM Tris-HCl at pH 8.0.

The apoE target was then amplified by transcription. An aliquot of the ethanol precipitated DNA was in vitro transcribed using the AMPLISCRIBE™ T7 transcription kit from Epicentre (Madison Wis.). The resulting transcription products were analyzed by agarose gel electrophoresis. RNA products of the expected size were observed only in SSP oligonucleotide extended genomic DNA, and were absent in controls from unprimed genomic DNA.

Gel electrophoresis of the following samples validated the method. Lane 1: 100 bp DNA marker; Lane 2: 10% of the T7 transcription reaction from 250 ng of lambda exonuclease treated, human genomic DNA; Lane 3: 10% of the T7 transcription reaction from 250 ng of lambda exonuclease treated, SSPP primer extended human genomic DNA; Lane 4: 10% of the T3 transcription reaction from same DNA as in Lane 3; Lane 5: 10% of the T7 transcription reaction from 60 ng of clone apoE DNA and treated as in Lane3; Lane 6: 10% of the T3 transcription reaction from same DNA as in Lane 5; Lane 7: 10% of the T7 transcription reaction from apoE clone, no treatment; Lane 8: 1 µg human genomic DNA, no treatment.

To confirm that in-vitro transcribed RNA is indeed apoE RNA, RT-PCR was performed according to the protocol provided by the vendor (THERMOSCRIPT™ RT PCR systems, Life Technologies, Bethesda, Md.). PCR using the primer pair, P3 and P6ASE (SEQ ID NO:2 and SEQ ID NO: 3), produced the correct size product, only for DNA derived from RNA transcribed from SSP oligonucleotide-extended genomic DNA. There is no PCR product derived from the RNA transcription mixture, suggesting the PCR product is not from unprimed genomic DNA. There is no PCR product when using the primer pair T7 and P6ASE (SEQ ID NO:4 and SEQ ID NO:3) confirming the PCR template is indeed cDNA derived from RNA.

Gel electrophoresis of controls and test reactions validated method. A specific amplified fragment was evident when human genomic DNA was used as the template with the appropriate primers. The amplified RNA was detected by PCR. Further, he PCR product was isolated from preparative agarose gel electrophoresis, and sequenced. DNA sequencing confirmed that the PCR product was indeed apoE.

These reactions and manipulations can be coupled and streamlined to achieve considerable gains in efficiency and economy.

EXAMPLE 5

SSAT is suited for multiplex reactions. In this example, multiple target fragments were amplified by site specific amplification by transcription. A 5.5 kb genomic human apoE serve as DNA target template in this manipulation. Briefly, apoE DNA is cleaved by restriction enzymes AvaI, BsrDl, and StuI (New England Biolabs, Beverly, Mass.) to generate eight DNA fragments. One of the eight DNA fragment is the same Stu1 fragment as described previously in Example 1. The human apoe sequence is available, e.g., from GenBank entry AF 261279.

The primer sequences listed in SEQ ID NOS:1 to 22 were used:

SEQ ID NO:1 (T7StuSE): AATTAATACG ACTCACTATA GGGAAGGCCT ACAAATCGGA ACTGGAG

SEQ ID NO:2 (P3): GAACAACTGA CCCCGGTGGCGG

SEQ ID NO:3 (P6ASE): GAGGCGAGGCGCACCCGC AG

SEQ ID NO:4 (T7): TTAATACGAC TCACTATAGG G

SEQ ID NO:5 (T7AvaSE2): CATTAATACGACTCACTATAGGGACTCGGGGTC GGGCTTGGGGAGA

SEQ ID NO:6 (T7AvaSE3): CATTAATACGACTCACTATAGGGACCCGGGAGA GGAAGATGGAATTTTC

SEQ ID NO:7 (T7AvaSE4): CATTAATACGACTCACTATAGGGACCCGAGCTGC GCCAGCAGACCGAG

SEQ ID NO:8 (T7BsrD1SE): CATTAATACGACTCACTATAGGGACATTGCAGGCA GATAGTGAATACC

SEQ ID NO:9 (T7stuSE2): CATTAATACGACTCACTATAGGGAAGGCCTGGG GCGAGCGGCT

SEQ ID NO:10 (T7StuSE3): CATTAATACGACTCACTATAGGGAAGGCCTTCCA GGCCCGCCTCAAGA

SEQ ID NO:11 (AvaSE2): CTCGGGGTCGGGCTTGGGG AGA

SEQ ID NO:12 (AvaSE3): CCCGGGAGAGGAAGATGG AATTTTC

SEQ ID NO:13 (AvaSE4): CCCGAGCTGCGCCAGCAGA CCGAG

SEQ ID NO:14(BsrD1ASE): CATTGCAGGCAGATAGTG AATACC

SEQ ID NO:15(StuSE2): AGGCCTGGGGCGAGCGGCT

SEQ ID NO:16(StuSE3): CCTTCCAGGCCCGCCTCA AGA

SEQ ID NO:17(AvaASE2): CCCAGTAGGTGCTCGATA AATG

SEQ ID NO:18(AvaASE3): AGAAGAGGGGGCCCAG GGTCTG
SEQ ID NO:19(AvaASE4): TGAGTCAGAAGGGAAGAG AGAGAG
SEQ ID NO:20(BsrD1ASE): AGCACAGGTGTGTGGCA CCATG
SEQ ID NO:21 (StuASE2): CTCGTCCAGGCGGTC GCGGGT
SEQ ID NO:22 (StuASE3): TCCACCCCAGGAGGACGG CTG

10 µg of a plasmid DNA containing the 5.5 kb human apoE gene was digested with 40 units of AvaI and 40 units of StuI for 4 hours at 37° C. Subsequently, 20 units of BsrD1 was added to the reaction mixture. Incubation was continued for an additional 2 hours at 65° C. The restriction digestion was quenched on ice apoE DNA fragments were purified by the mini-elute enzyme clean-up kit (QIAGEN Inc.). An aliquot of 2 µg of the restricted DNA was treated with 2 units of lambda exonuclease at 37° C. for 30 minutes. The exonuclease reaction was terminated and inactivated by incubation at 80° C. for 15 minutes. The reaction mixture was adjusted to contain 2.5 M ammonium acetate, and precipitated by the addition of 2.5 volumes of 100% ethanol. The resulting mixture was then incubated on ice for two hours, and then centrifuge at room temperature at 16,000×g for 15 minutes in a Beckman ALLEGRA™ microcentrifuge to pellet the DNA. The ethanol supernatant was removed by pipetting, and the DNA pellet was rinsed with 70% ethanol, air dried, and dissolve in sterile MILLIO™ water (Millipore Corp, Billerica, Mass.).

Primer annealing was carried out in 30 µl containing 1× Klenow (3'-5'exo') buffer, 50 pmols of each T7apoE sequence primers (SEQ ID NO: 1, 5, 6, 7, 8, 9 and 10) and 1.8 µg of the lambda exonuclease treated DNA. The reaction mixture was heated at 75° C. for 5 minutes, followed by incubation at 37° C. for another 10 minutes. The annealing mixture was then diluted to 50 µl 1 with 1× Klenow buffer in the presence of 1 mM dNTPs and 10 units of Klenow enzyme (3'-5' exo) for 1 hour at 37° C. The extension reaction was terminated by heating at 75° C. for 20 minutes to inactivate the enzyme. Excess T7apoE sequence primers were removed by Exonulease1 (Amersham Pharmacia Inc.). Exonuclease1 was removed by the mini-elute enzyme purification kit as described earlier.

To detect the SSP oligonucleotide-extended product, an aliquot of the treated DNA was in vitro transcribed using the AMPLISCRIBE™ T7 transcription kit from Epicentre, (Madison, Wis.). The RNA was then reverse transcribed into cDNA using antisense apoE primers specific for each of the seven restriction fragments (SEQ ID NO:3, 17, 18, 19, 20, 21 & 22, respectively). Only the RNA which includes the corresponding sense strand of the apoE reverse transcription primer sequences were reverse transcribed into cDNA. cDNA synthesis reaction was carried out according to the protocol of the THERMOSCRIPT™ RT PCR system (Life Technologies, Bethesda, Md.). PCR reactions were carried out in 20 µl volume, in an Eppendoff DNA thermocycler, using AMPLITAG™.

Gold DNA polymerase and apoE sequence primer pairs which are specific for the seven target restriction fragments (SEQ ID NO:2,3,11–22.). A PCR assay detected amplified products from all RNA-amplified apoE fragments: AvaI-2, AvaI-3, AvaI-4, BsrD1, StuI-1, StuI-2, and StuI-3. All seven primer pairs amplified a prominent band of the expected size from cDNA but not from RNA. DNA sequencing of five representative fragments confirmed that they are all correct apoE sequences.

EXAMPLE 6

Solid Phase Based Amplification

This example illustrates solid-phase sequence specific amplification by transcription. The StuI fragment of human apolipoprotein E gene (encoding amino acid 72 to amino acid 209) is the test substrate model. The following primer sequences were used: SEQ D NO: 2, SEQ ID NO: 3, and SEQ ID NO: 23.

Streptavidin coated microplates (NoAb Biodiscoveries, Mississauga, Ontario, Canada) were used to immobilize 5' end biotin labeled, SSSP oligonucleotide oligonucleotide (BT7StuSE1). Briefly, oligos were diluted to 100 µl with TBS (Tris-Buffered Saline, 20 mM Tris, 500 mM sodium chloride, pH 7.5), and spotted into 8-well strips. Each well contained either 50 pmols or 5 pmols of BT7StuSE1. The negative-control well contained 50 pmols of T7StuSE1 oligo (SEQ ID NO: 1) primer. After a two hour incubation at room temperature, oligonucleotide solutions were discarded, and the wells were rinsed several times with 100 µl TBS, 0.01% Tween 20, followed by incubation at room temperature for 30 minutes with a blocking solution of TBS, 0.01% Tween 20 and 100 µg/ml BSA (New England Biolabs, Beverly, Mass.). The wells were then rinse twice, with 100 µl TBS followed by 100 µl of Klenow buffer (3'-5' exo). Single-stranded DNA were created by lambda exonuclease digestion of the restricted human Apo E fragments, as previously described in examples 1 and 2. 1 µg of the single-stranded DNA was annealed to the immobilized primers for 15 minutes at 37° C. in 30 µl of Klenow buffer, followed by primer-extension in 100 µl reaction volume that contained Klenow buffer, 1 mM dNTPs, and 20 units of Klenow DNA polymerase (3'-5' exo). Enzyme incubation was for one hour at 37° C. in a humidity chamber. The wells were then washed several times with 200 µl of sterile 10 mM Tris-HCl, pH 8.0, and once, with 50 µl 1×T7 RNA polymerase transcription buffer. In-vitro transcription was carried out in 20 µl at 37° C. for two hours using the T7 AMPLISCRIBE™ kit from Epicentre Technologies (Madison, Wis.). The resulting transcription products were analyzed by agarose gel electrophoresis. RNA product of the expected size was observed only in wells, which contained immobilized Bt7StuSE1 primer, and is absent from the well which contained the T7StuI oligonucleotide primer. Furthermore, repeatable, robust transcription was maintained over a period of several days of storage at 4° C. After an initial round of transcription, the insoluble support was stored at least for 24 hours, and then removed for further transcription. Five such reactions over a storage period of ten days provided continued amplification with no loss in yield.

To confirm the in-vitro transcribed RNA is indeed apoE RNA, RT-PCR was performed according to the protocol provided by THERMOSCRIPT™ RT PCR systems (Life Technologies, Bethesda, Md.). To confirm the PCR product is indeed apoE sequence, the PCR product was isolated from preparative agarose gel electrophoresis and sequenced. DNA sequencing confirmed the PCR product was indeed apoE.

EXAMPLE 7

Human whole genomic DNA was treated with lambda exonucleases, hybridized to SSP primers attached to an insoluble support, extended using a DNA polymerase, then amplified in accordance with the single promoter SP-TCR method. Robust transcription was observed using input human genomic DNA in an amount between 100 ng and 2 µg. The detection of RNA amplified transcripts from the long sample is indicative of the unexpected amplification yield provided by the method. No RNA amplified products were detected in a negative control reaction. The reaction product migrated as a discrete band on agarose gel.

EXAMPLE 8

Materials for this example included:

mRNA: Human liver Poly A RNA purchased from Ambion Inc., Austin, Tx.

Anchor primer: Bt-T7d(T)$_{17}$V where Bt=5'biotin; T7=T7 RNA polymerase promoter; d (T) 17=a homopolymner of 17 T residue; V=A, G, and C. This primer has the sequence: 5'-TTAATACGACTCACTATAGGGTTTT TTTTTV-3' (SEQ ID NO:26)

Solid phase: streptavidin coated wells (NoAb Biodiscoveries, Mississauga, Ontario, Canada)

The procedure was as follows:

1. 200 pmol Anchor Primer was attached each streptavidin coated well,
2. Wells were washed with TBS and rinsed with 1× first strand synthesis buffer,
3. 2 µg human liver mRNA (Ambion, Inc. Austin, Tex.) was annealed to anchored oligos in the presence of first strand synthesis buffer, and DNase inhibitor (Universal Riboclone cDNA Synthesis System Catalog No. C4360, Promega Corp, Madison, Wis., USA). Kanamycin mRNA(Promega Corp) was used as a positive control (1 µg per reaction). The negative control was a well to which no RNA was added. mRNAs were annealed at 42° C. for 5 minutes.
4. cDNA synthesis was initiatedby adding sodium pyrophosphate, and AMV reverse transcriptase (All reagents from Promega Catalog No. C4360). The final concentrations for all the components were: 1× first strand synthesis buffer (5 mM Tris-HCL, pH 8.3 at 42 degree C.; 50 mM KCL; 10 mM MgCl2; 0.5 mM spermidine; 10 mM DTT; 1 mM each dATP, dCTP, dGTP, dTTP); 40 units of Rnasin ribonuclease inhibitor; 4 mM sodium pyrophosphate and 30 units of AMV reverse transcriptase. The final volume of first strand cDNA synthesis reaction was 20 µl.
5. Reactions were incubated at 42° C. for 1 hour.
6. Second strand cDNA synthesis was initiated by the addition of 40 µl of 2.5× second strand synthesis buffer (1×=40 mM Tris-HCL, pH 7.2); 5 µl of 1 mg/ml acetylated BSA; 23 units of DNA polymerase 1; 0.8 unit of RNase H, and nuclease free water to final volume of 100 µl. Incubate at 14–16° C. for 2 hours.
7. 2 units of T4 DNA polymerase/µg of input RNA was added. Incubation was continued at 37° C. for 10 minutes.
8. Wells were washed several times with 50 mM Tris-HCL, pH 8.0. The wells were placed on ice, and 20 µl 1× T7 RNA polymerase transcription buffer was added.
9. Transcription reactions were performed in 20 µl volume, by following protocol provided by the manufacturer (AMPLISCRIBE™ T7 high yield transcription kit, Cat# AS2607, Epicentre, Madison, Wis.). Reactions were incubated at 37° C. for 1–2 hours.
10. 5 µl of the reactions was analyzed on an agarose gel.

Results: A distribution of nucleic acid fragments corresponding to RNA transcripts of >0.4 kb, with a medium distribution between 0.4–1.0 kb were observed in both reaction primed by human liver mRNA primed cDNA library, and the reaction primed by kanamycin resistance gene mRNA. No RNA transcripts were detected from the negative control.

Nucleic acid was amplified by RT-PCR from the transcription reaction product produced from the insoluble substrate. Specific size fragments corresponding to mRNAs for human serum albumin, beta-actin, and G3PDH were detected in the sample derived from the human liver mRNA sample, but not from the control sample of mRNA for the kanamycin resistance gene. Similarly, a nucleic acid fragment for the kanamycin resistance gene was detected in this control, whereas the liver specific transcripts were not. This example demonstrated that mRNA can be amplified from an insoluble support prepared as described.

EXAMPLE 9

Materials for this example included:

mRNA: Human liver total RNA, and yeast RNA (Ambion Inc., Austin Tex.). Kanamycin resistance gene control mRNA (Promega Corp).

Anchor primers: 1) Bt-T7d(T)$_{17}$V (see above). 2) Bt-ASC 1T3 where Bt=5' biotin; T3=T3 promoter sequence; ASC1= restriction endonuclease recognition site for AscI (GGCGCGCC). 3) TCR-adapter Solid phase: streptavidin coated wells (NoAb Biodiscoveries, Mississauga, Ontario, Canada)

The first part of the procedure was as follows:

1. 200 pmol Anchor Primer was attached each streptavidin coated well,
2. Wells were washed with TBS and rinse with 1× first strand synthesis buffer,
3. Samples were annealed to anchored oligos in the presence of first strand synthesis buffer, and DNase inhibitor (Universal Riboclone cDNA Synthesis System Catalog No. C4360, Promega Corp, Madison Wis.). Four separate reactions were set up. The reaction samples were: (a) 20 µg human liver total RNA; (b) 20 µg human liver total RNA+1 ng kanamycin mRNA; (c) 20 µg human liver total RNA+10 ng kanamycin mRNA; and (d) 20 µg yeast RNA+100 ng kanamycin mRNA K. mRNAs were annealed at 42° C. for 5 minutes.
4. cDNA synthesis was initiated by adding sodium pyrophosphate, and AMV reverse transcriptase (All reagents from Promega Catalog No. C4360). The final concentrations for all the components were: 1× first strand synthesis buffer (50 mM Tris-HCL, pH 8.3 at 42 degree C.; 50 mM KCL; 10 mM MgCl2; 0.5 mM spermidine; 10 mM DTT; 1 mM each dATP, dCTP, dGTP, dTTP); 40 units of Rnasin ribonuclease inhibitor; 4 mM sodium pyrophosphate and 30 units of AMV reverse transcriptase. The final volume of first strand cDNA synthesis reaction was 20 µl.
5. Reactions were incubated at 42° C. for 1 hour.
6. Second strand cDNA synthesis was initiated by the addition of 40 µl of 2.5× second strand synthesis buffer (1×=40 mM Tris-HCL, pH 7.2); 5 µl of 1 mg/ml acetylated BSA; 23 units of DNA polymerase 1; 0.8 unit of DNase H, and nuclease free water to final volume of 100 µl. Incubate at 14–16 degree C. for 2 hours.
7. 2 units of T4 DNA polymerase/ug of input RNA were added. Incubation was continued at 37° C. for 10 minutes.

8. Wells were washed several times with 50 mM Tris-HCL, pH 8.0.
9. TCR-Adapter ligation: Adapter ligation was performed in 30 ul volume using the Fast-link DNA ligation kit (Epicentre Cat#LK0750H, Madison Wis.). The final concentration of all the components were: 1× ligation buffer (33 mM Tris-acetate pH 7.8, 66 mM potassium acetate, 10 mM magnesium acetate, 5 mM DTT); 05 mM ATP; 20 pmol TCR-adapter. Incubate at room temperature for 30 minutes, and wash well several times with 50 mM Tris-HCL pH 8.0 followed by 20 $\mu$l of 1×T7 transcription buffer.
10. Transcription reactions were performed in 20 $\mu$l volume following the protocol provided by the manufacturer (AMPLISCRIBE™ T7 high yield transcription kit, Cat# AS2607, Epicentre, Madison, Wis.). Reactions were incubated at 37° C. for 1–2 hours.
11. 4 $\mu$l of each reaction were analyzed on an agarose gel.

Result: The following RNA amplification products were observed: RNA transcripts
>0.4 kb in length, with a medium distribution between 0.4–1.0 kb were observed in all reactions that amplified human liver total RNA spiked with 0, 1, or 10 ng of kanamycin mRNA), and a discrete RNA band was observed in reaction #4 which is derived from the control mRNA for the kanamycin resistance gene.

These findings indicate that a cDNA library can be synthesized on an insoluble substrate from 20 $\mu$g of input human total RNA (which corresponds to approximately 200–400 ng of mRNA). The library can be amplified by transcription.

An individual species of 1 ng or less can be detected by this method as demonstrated by detection of the spiked RNA for the kanamycin resistance gene. Further, the library was stored for several days under refrigeration. The stored library was effectively transcribed, thus verifying the value of this technique for archiving RNA populations. It was also found that the stored library could be effectively transcribed after two or more months of storage.

EXAMPLE 10

RNA (16 $\mu$l) from the first T7 transcription (Example 6) was precipitated with ethanol and redissolved in 20 $\mu$l of nuclease-free water. 4 $\mu$l of RNA were used for T3 transcription cycling (TCR). The experimental procedures were as follows:

1. 200 pmol of the Bt-T3ASCI oligonucleotide was attached to streptavidin coated wells
2. Wells were washed with TBS and rinsed with 1× first strand synthesis buffer
3. The mRNA was annealed to the anchored oligonucleotides in the presence of first strand synthesis buffer, and DNase inhibitor. A total of 4 reactions were set-up as follows:
   a) 4 $\mu$g RNA from T7 reaction 1 of Example 6;
   b) 4 $\mu$g RNA from T7 reaction 2 of Example 6
   c) 4 $\mu$g RNA from T7 reaction 3 of Example 6
   d) 4 $\mu$g RNA from T7 reaction 4 of Example 6
   Annealing was performed at 42° C. for 5 minutes.
4. cDNA synthesis was initiated by adding sodium pyrophosphate, and AMV reverse transcriptase. The final concentrations for all the components was: 1× first strand synthesis buffer (50 mM Tris-HCL, pH 8.3 at 42° C.; 50 mM KCL; 10 mM MgCl$_2$; 0.5 mM spermidine; 10 mM DTT; 1 mM each dATP, dCTP, dGTP, dTTP); 40 units of Rnasin ribonuclease inhibitor; 4 mM sodium pyrophosphate and 30 units of AMV reverse transcriptase. The final volume of the first strand cDNA synthesis reaction was 20 $\mu$l.
5. The reaction was incubated at 42° C. for 1 hour.
6. Second strand cDNA synthesis was effected by the addition of 40 $\mu$l of 2.5× second strand synthesis buffer (1×=40 mM Tris-HCL, pH 7.2); 5 ul of 1 mg/ml acetylated BSA; 23 units of DNA polymerase 1; 0.8 unit of DNase H, and nuclease free water to final volume of 100 $\mu$l. Incubate at 14–16° C. for 2 hours.
7. Then 2 $\mu$l (6 units) of *E. coli* ligase was added to each well, and the incubation was extended for 30 minutes at 16° C.
8. 2 units of T4 DNA polymerase/$\mu$g of input RNA was added to each well, and the incubation was extended for 10 minutes at 37° C.
9. After the incubation, wells were washed several times with 50 mM Tris-HCL, pH 8.0.
10. Then transcription was used to amplify RNA from each well. Transcription reactions were performed in 20 $\mu$l following the protocol of AMPLISCRIBE™ T3 High Yield Transcription Kit, (Cat# AS2603, Epicentre, Madison Wis.). Reactions were incubated at 37° C. for 1–2 hours.
11. The reaction was analyzed by agarose gel electrophoresis.

Results: Transcription products having a size of 0.4–1 kb were observed in all 4 reactions. These results demonstrated the TCR adapter ligated to the ends of the T7d(T)$_{17}$V primed cDNA from Example 9 was effective for driving T3 DNA polymerase mediated amplification. This example is a successful application of the so-called Transcription Chain Reaction (TCR) method.

The incorporation of a rare sequence cutter restriction enzyme such as AscI (which cuts human DNA on average once per 670,000 base pairs) permitted the release of the anchored library cDNA from the insoluble support, thereby providing flexibility in downstream applications. It was also found that three full cycles of TCR amplification had an amplification power of greater than $10^8$, and that 1 ng of total RNA was successfully amplified.

EXAMPLE 11

An exemplary dG tailing procedure is as following:
1. Immobilize Bt12T7d(T)20V anchor primer
2. Anneal total RNA
3. First strand synthesis as described
4. Rinse three times with 50 mM Tris-HCL (pH 8.0), followed by rinsing with terminal transferase buffer.
5. Add terminal transferase buffer, 25 1M dGTP, 10 units of terminal transferase in 20 $\mu$l reaction, and incubate at 37° C. for 15 minutes
6. Wash wells and proceed to Tag annealing Tag annealing and second strand synthesis:
1. Combine 20 pmol Tag (LITP-1) in 20 $\mu$l EcoPoll buffer (New England Biolabs, Beverly, Mass.), and incubate at 37° C. for 10 minutes
2. Add dNTPs to final 1 mM; 5 ug nuclease free BSA; 0.8 units of RnaseH, and 1 unit of Klenow enzyme in final volume of 50 $\mu$l. Incubate for 1 hour at 37° C.

Transcription of the immobilized template produced by this method is as described.

A number of embodiments of the invention have been described. Nevertheless, it will be understood that various modifications may be made without departing from the spirit and scope of the invention. Accordingly, other embodiments are within the scope of the following claims.

What is claimed is:

1. An insoluble support comprising a plurality of attached oligonucleotides, wherein (a) the attached oligonucleotides comprise a prokaryotic promoter sequence and a target annealing sequence, (b) the target annealing sequence is 3' of the promoter, (c) the oligonucleotide has an extendable 3' terminus; (d) the proximal end of the promoter sequence is spaced from the insoluble support by a distance greater than 10 nm; and (e) the attached oligonucleotides are covalently attached to the insoluble support by a polyethylene glycol linker which has between 8 and 16 units.

2. The support of claim 1 wherein the oligonucleotides are less than 80 nucleotides in length.

3. The support of claim 1 wherein each target annealing sequence of the plurality is the same and the target annealing sequence can anneal to a plurality of different target sequences.

4. The support of claim 3 wherein the target annealing sequence comprises a poly-thymidine tract.

5. The support of claim 1 wherein each target annealing sequence of the plurality comprises a poly-thymidine tract and/has a 3' A, G, or C.

6. An insoluble support comprising attached template nucleic acids, wherein (a) each attached template nucleic acids comprise a prokaryotic promoter sequence and a target sequence, (b) for each template nucleic acid, the promoter is located between the target sequence and the site that attaches the template nucleic acid to the support, (c) the template nucleic acids can be transcibed to produce RNA copies of each respective target sequence, and (d) the template nucleic acids is spaced from the support by a nucleotide-free linker that includes an identical number of main chain atoms as a polyethylene glycol linker that has between 8 and 16 uniuts.

7. The support of claim 6 wherein the template nucleic acids correspond to nucleic acids in a biological sample.

8. The support of claim 7 wherein the template nucleic acids correspond to eukaryotic mRNAs.

9. The support of claim 6 wherein a plurality of the template nucleic acids each comprises a common adaptor sequence at thier respective distal ends.

10. The support of claim 1 or 6 wherein the support is a rigid planar support.

11. The support of claim 1 or 6 wherein the support is a membrane in a spin cup.

* * * * *

SEQUENCE LISTING

<160> NUMBER OF SEQ ID NOS: 35

<210> SEQ ID NO 1
<211> LENGTH: 47
<212> TYPE: DNA
<213> ORGANISM: Artificial Sequence
<220> FEATURE:
<223> OTHER INFORMATION: Synthetically generated oligonucleotide

<400> SEQUENCE: 1
aattaatacg actcactata gggaaggcct acaaatcgga actggag      47

<210> SEQ ID NO 2
<211> LENGTH: 22
<212> TYPE: DNA
<213> ORGANISM: Artificial Sequence
<220> FEATURE:
<223> OTHER INFORMATION: Synthetically generated oligonucleotide

<400> SEQUENCE: 2
gaacaactga ccccggtggc gg      22

<210> SEQ ID NO 3
<211> LENGTH: 20
<212> TYPE: DNA
<213> ORGANISM: Artificial Sequence
<220> FEATURE:
<223> OTHER INFORMATION: Synthetically generated oligonucleotide

<400> SEQUENCE: 3
gaggcgaggc gcacccgcag      20

<210> SEQ ID NO 4
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 4
ttaatacgac tcactatagg g      21

<210> SEQ ID NO 5
<211> LENGTH: 46
<212> TYPE: DNA
<213> ORGANISM: Artificial Sequence
<220> FEATURE:
<223> OTHER INFORMATION: Synthetically generated oligonucleotide

<400> SEQUENCE: 5
cattaatacg actcactata gggactcggg gtcgggcttg gggaga      46

<210> SEQ ID NO 6
<211> LENGTH: 49
<212> TYPE: DNA
<213> ORGANISM: Artificial Sequence
<220> FEATURE:
<223> OTHER INFORMATION: Synthetically generated oligonucleotide

<400> SEQUENCE: 6
cattaatacg actcactata gggacccggg agaggaagat ggaattttc      49

<210> SEQ ID NO 7
<211> LENGTH: 48

```
<210> SEQ ID NO 7
<211> LENGTH: 48
<212> TYPE: DNA
<213> ORGANISM: Artificial Sequence
<220> FEATURE:
<223> OTHER INFORMATION: Synthetically generated oligonucleotide

<400> SEQUENCE: 7
cattaatacg actcactata gggacccgag ctgcgccagc agaccgag           48

<210> SEQ ID NO 8
<211> LENGTH: 48
<212> TYPE: DNA
<213> ORGANISM: Artificial Sequence
<220> FEATURE:
<223> OTHER INFORMATION: Synthetically generated oligonucleotide

<400> SEQUENCE: 8
cattaatacg actcactata gggacattgc aggcagatag tgaatacc           48

<210> SEQ ID NO 9
<211> LENGTH: 43
<212> TYPE: DNA
<213> ORGANISM: Artificial Sequence
<220> FEATURE:
<223> OTHER INFORMATION: Synthetically generated oligonucleotide

<400> SEQUENCE: 9
cattaatacg actcactata gggaaggcct ggggcgagcg gct                43

<210> SEQ ID NO 10
<211> LENGTH: 48
<212> TYPE: DNA
<213> ORGANISM: Artificial Sequence
<220> FEATURE:
<223> OTHER INFORMATION: Synthetically generated oligonucleotide

<400> SEQUENCE: 10
cattaatacg actcactata gggaaggcct tccaggcccg cctcaaga           48

<210> SEQ ID NO 11
<211> LENGTH: 22
<212> TYPE: DNA
<213> ORGANISM: Artificial Sequence
<220> FEATURE:
<223> OTHER INFORMATION: Synthetically generated oligonucleotide

<400> SEQUENCE: 11
ctcggggtcg ggcttgggga ga                                       22

<210> SEQ ID NO 12
<211> LENGTH: 25
<212> TYPE: DNA
<213> ORGANISM: Artificial Sequence
<220> FEATURE:
<223> OTHER INFORMATION: Synthetically generated oligonucleotide

<400> SEQUENCE: 12
cccgggagag gaagatggaa ttttc                                    25

<210> SEQ ID NO 13
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 13
```

```
cccgagctgc gccagcagac cgag                                          24
```

<210> SEQ ID NO 14
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 14

```
cattgcaggc agatagtgaa tacc                                          24
```

<210> SEQ ID NO 15
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 15

```
aggcctgggg cgagcggct                                                19
```

<210> SEQ ID NO 16
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 16

```
ccttccaggc ccgcctcaag a                                             21
```

<210> SEQ ID NO 17
<211> LENGTH: 22
<212> TYPE: DNA
<213> ORGANISM: Artificial Sequence
<220> FEATURE:
<223> OTHER INFORMATION: Synthetically generated oligonucleotide

<400> SEQUENCE: 17

```
cccagtaggt gctcgataaa tg                                            22
```

<210> SEQ ID NO 18
<211> LENGTH: 22
<212> TYPE: DNA
<213> ORGANISM: Artificial Sequence
<220> FEATURE:
<223> OTHER INFORMATION: Synthetically generated oligonucleotide

<400> SEQUENCE: 18

```
agaagagggg gcccagggtc tg                                            22
```

<210> SEQ ID NO 19
<211> LENGTH: 24
<212> TYPE: DNA
<213> ORGANISM: Artificial Sequence
<220> FEATURE:
<223> OTHER INFORMATION: Synthetically generated oligonucleotide

<400> SEQUENCE: 19

```
tgagtcagaa gggaagagag agag                                          24
```

<210> SEQ ID NO 20
<211> LENGTH: 22
<212> TYPE: DNA
<213> ORGANISM: Artificial Sequence

```
<220> FEATURE:
<223> OTHER INFORMATION: Synthetically generated oligonucleotide

<400> SEQUENCE: 20
agcacaggtg tgtggcacca tg                                            22

<210> SEQ ID NO 21
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 21
ctcgtccagg cggtcgcggg t                                             21

<210> SEQ ID NO 22
<211> LENGTH: 21
<212> TYPE: DNA
<213> ORGANISM: Artificial Sequence
<220> FEATURE:
<223> OTHER INFORMATION: Synthetically generated oligonucleotide

<400> SEQUENCE: 22
tccaccccag gaggacggct g                                             21

<210> SEQ ID NO 23
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 23
taatacgact cactatagg                                                19

<210> SEQ ID NO 24
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 24
aattaaccct cactaaagg                                                19

<210> SEQ ID NO 25
<211> LENGTH: 19
<212> TYPE: DNA
<213> ORGANISM: Artificial Sequence
<220> FEATURE:
<223> OTHER INFORMATION: Synthetically generated oligonucleotide

<400> SEQUENCE: 25
atttaggtga cactataga                                                19

<210> SEQ ID NO 26
<211> LENGTH: 39
<212> TYPE: DNA
<213> ORGANISM: Artificial Sequence
<220> FEATURE:
<223> OTHER INFORMATION: Synthetically generated oligonucleotide

<400> SEQUENCE: 26
ttaatacgac tcactatagg gttttttttt ttttttttv                          39
```

<210> SEQ ID NO 27
<211> LENGTH: 33
<212> TYPE: DNA
<213> ORGANISM: Artificial Sequence
<220> FEATURE:
<223> OTHER INFORMATION: Synthetically generated oligonucleotide

<400> SEQUENCE: 27
gcgccaatta tcgaaaaaaa aaaaaaaaaa aaa                           33

<210> SEQ ID NO 28
<211> LENGTH: 58
<212> TYPE: DNA
<213> ORGANISM: Artificial Sequence
<220> FEATURE:
<223> OTHER INFORMATION: Synthetically generated oligonucleotide

<400> SEQUENCE: 28
ataggcgcgc caattaatac gactcactat agggagattt tttttttttt tttttttv    58

<210> SEQ ID NO 29
<211> LENGTH: 58
<212> TYPE: DNA
<213> ORGANISM: Artificial Sequence
<220> FEATURE:
<223> OTHER INFORMATION: Synthetically generated oligonucleotide

<400> SEQUENCE: 29
ataggcgcgc caattaatac gactcactat agggagattt tttttttttt tttttttv    58

<210> SEQ ID NO 30
<211> LENGTH: 71
<212> TYPE: DNA
<213> ORGANISM: Artificial Sequence
<220> FEATURE:
<223> OTHER INFORMATION: Synthetically generated oligonucleotide

<400> SEQUENCE: 30
acgtacgtac gtcataggcg cgccaattaa tacgactcac tatagggaga tttttttttt    60
tttttttttt v                                                        71

<210> SEQ ID NO 31
<211> LENGTH: 96
<212> TYPE: DNA
<213> ORGANISM: Artificial Sequence
<220> FEATURE:
<223> OTHER INFORMATION: Synthetically generated oligonucleotide

<400> SEQUENCE: 31
acgtacgtac gtacgtacgt acgtcacgta cgtacgtcat aggcgcgcca attaatacga    60
ctcactatag ggagattttt tttttttttt tttttv                            96

<210> SEQ ID NO 32
<211> LENGTH: 33
<212> TYPE: DNA
<213> ORGANISM: Artificial Sequence
<220> FEATURE:
<223> OTHER INFORMATION: Synthetically generated oligonucleotide

<400> SEQUENCE: 32
gcgccaatta tcgaaaaaaa aaaaaaaaaa aaa                                33

<210> SEQ ID NO 33
<211> LENGTH: 46

```
-continued

<212> TYPE: DNA
<213> ORGANISM: Artificial Sequence
<220> FEATURE:
<223> OTHER INFORMATION: Synthetically generated oligonucleotide

<400> SEQUENCE: 33
attaatacga ctcactatag ggagattttt tttttttttt tttttv                    46

<210> SEQ ID NO 34
<211> LENGTH: 52
<212> TYPE: DNA
<213> ORGANISM: Artificial Sequence
<220> FEATURE:
<223> OTHER INFORMATION: Synthetically generated oligonucleotide

<400> SEQUENCE: 34
gcgccaatta atacgactca ctatagggag attttttttt tttttttttt tv             52

<210> SEQ ID NO 35
<211> LENGTH: 58
<212> TYPE: DNA
<213> ORGANISM: Artificial Sequence
<220> FEATURE:
<223> OTHER INFORMATION: Synthetically generated oligonucleotide

<400> SEQUENCE: 35
ataggcgcgc caattaatac gactcactat agggagattt tttttttttt tttttttv       58
```